(12) United States Patent
Tan et al.

(10) Patent No.: US 10,676,488 B2
(45) Date of Patent: Jun. 9, 2020

(54) MULTIFUNCTIONAL SUPRAMOLECULAR HYBRIDS ENCOMPASSING HIERARCHICAL SELF-ORDERING OF METAL-ORGANIC FRAMEWORK NANOPARTICLES AND METHOD OF PREPARING SAME

(71) Applicant: Samsung Electronics Co., Ltd., Suwon-si, Gyeonggi-do (KR)

(72) Inventors: Jin-Chong Tan, Oxford (GB); Abhijeet K. Chaudhari, Oxford (GB)

(73) Assignees: Samsung Electronics Co., Ltd., Gyeonggi-do (KR); University Oxford Innovation Limited, Oxford (GB)

( * ) Notice: Subject to any disclaimer, the term of this patent is extended or adjusted under 35 U.S.C. 154(b) by 61 days.

(21) Appl. No.: 14/961,961

(22) Filed: Dec. 8, 2015

(65) Prior Publication Data

US 2016/0159822 A1 Jun. 9, 2016

(30) Foreign Application Priority Data

Dec. 8, 2014 (KR) .................. 10-2014-0174904
Dec. 7, 2015 (JP) .................. 2015-238765

(51) Int. Cl.
*C07F 1/08* (2006.01)
*C07C 63/307* (2006.01)
*C08G 83/00* (2006.01)
*C07C 51/41* (2006.01)

(52) U.S. Cl.
CPC .............. *C07F 1/08* (2013.01); *C07C 51/418* (2013.01); *C07C 63/307* (2013.01); *C08G 83/008* (2013.01)

(58) Field of Classification Search
CPC ........ C07C 63/307; C07C 51/418; C07F 1/08
See application file for complete search history.

(56) References Cited

U.S. PATENT DOCUMENTS

| 7,553,352 | B2 | 6/2009 | Mueller et al. |
| 988,739 | A1 | 6/2011 | Mueier et al. |
| 8,115,024 | B2 | 2/2012 | Schubert et al. |
| 8,163,949 | B2 | 4/2012 | Mueller et al. |
| 8,309,681 | B2 | 11/2012 | Koh Et Ai |
| 8,324,323 | B2 | 12/2012 | Koh et al. |
| 8,372,998 | B2 | 2/2013 | Schubert et al. |
| 8,884,087 | B2 | 11/2014 | Koh et al. |
| 9,186,651 | B2 | 11/2015 | da Silva Pinto et al. |
| 2009/0042000 | A1* | 2/2009 | Schubert ............... C07C 51/418 428/219 |
| 2012/0091064 | A1 | 4/2012 | Schubert et al. |
| 2014/0045074 | A1 | 2/2014 | Wiers et al. |
| 2014/0194639 | A1 | 7/2014 | Chen et al. |
| 2014/0208650 | A1 | 7/2014 | Gaab et al. |

FOREIGN PATENT DOCUMENTS

| CN | 102030767 A | 4/2011 |
| CN | 103394336 A | 11/2013 |
| CN | 103756646 A | 4/2014 |
| CN | 103785363 A | 5/2014 |
| CN | 103787875 A | 5/2014 |
| JP | 2007038848 A | 11/2007 |
| JP | 2012519171 A | 8/2012 |
| KR | 10-2008-0103986 A | 11/2008 |
| KR | 10-2014-0002837 A | 1/2014 |
| WO | WO-2012027538 A2 | 3/2012 |

OTHER PUBLICATIONS

Peng (Nature Communications; Jul. 22, 2014; pp. 1-7).*
Liu (CN 103787875 (A); May 2014; machine translation).*
Ezekiel (Chemical Science Transactions; 2013, 2(4), 1386-1394).*
Shaozhou Li et al., Facile growth of a single-crystal pattern: a case study of HKUST-1, Chem. Comm., vol. 48, p. 11901-11903, 2012.
First Office Action from the Patent Office of the People's Republic of China for CN 201510898245.5 dated Dec. 18, 2018, and it's English language translation.
Yunpan, Y. et al., "Solvent effect on catalytic properties of microstructures in metal-organic frameworks," Journal of Chemical Industry and Engineering, vol. 65, No. 5, May 2014, pp. 1652-1659, only abstract consider.
Jilin Univerity Press, Oct. 2013, 1st Edition and its English language translation, only abstract considered.
Katharina Peikert et al., "Amino Substituted Cu3(btc)2: a new metal-organic framework with a versatile functionality", Chem. Commun. vol. 48, pp. 1196-11198 (2012).
Stephen S. et al., "A Chemically Functionalizable Nanoporous Material [Cu3(TMA)2(H20)3]n" Science Mag, vol. 283, pp. 1148-1150 (1999).
Rob Ameloot et al., "INterfacial synthesis of hollow metal-organic framework capsules demonstrating selective permeability" Nature Chemistry, vol. 3, p. 382-387, May 2011.
Haiqiang Du et al., "A hierarchical supra-nanostructure of HKUST-1 featuring enhanced $H_2$ adsorption enthalpy and higher mesoporosity" Cryst. Eng. Comm., vol. 13 p. 3314-3316, 2011.
Maria Klimakow et al., "Mechanochemical Synthesis of Metal-Organic Frameworks: A Fast and Facile Approach toward Quantitative Yields and High Specific Surface Areas" Chemistry of Materials Article, American Chemical Society, vol. 22, p. 5216-5221, 2010.
Fang Zou et al., "Microwave-Assisted Synthesis of HKUST-1 and Functionalized HKUST-1@$H_3PW_{12}O_{40}$: Selective Adsorption of Heavy Metal Ions in Water Analyzed with Synchrotron Radiation"ChemPhysChem, vol. 14, pp. 2825-2832, 2013.
Jin-Liang Zhuang et al., "Rapid Room-Temperature Synthesis of Metal-Organic Framework HKUST-1 Crystals in Bulk and as Oriented and Patterened Thin Films", Advanced Functional Materials, vol. 21 p. 1442-1447, 2011.

(Continued)

*Primary Examiner* — Pancham Bakshi
(74) *Attorney, Agent, or Firm* — Harness, Dickey & Pierce, P.L.C.

(57) ABSTRACT

A supramolecular metal-organic framework material is a reaction product of a copper compound, a trialkylamine represented by Chemical Formula 1, and benzene substituted with 3 or more carboxyl groups.

20 Claims, 36 Drawing Sheets

(56) References Cited

OTHER PUBLICATIONS

Omar M. Yaghi et al., "Reticular synthesis and the design of new materials", Nature Publishing Group, vol. 4223, p. 705-714, Jun. 2003.
Susumu Kitagawa et al., "Functional Porous Coordination Polymers", Angew. Chem. Int. Ed., vol. 43, p. 2334-2375, 2004.
Gérard Férey, "Hybrid porous solids: past, present, future" Chem. Soc. Rev., vol. 37, p. 191-214, 2008.
Alexander U. Czaja et al., "Industrial applications of metal-organic frameworks" Chem. Soc. Rev., vol. 38, p. 1284-1293, 2009.
Anthony K. Cheetham et al., "Structural diversity and chemical trends in hybrid inorganic-organic framework materials" Chem. Comm. p. 4780-4785, 2006.
Seda Keskin et al., "Selecting metal organic frameworks as enabling materials in mixed matrix membranes for high efficiency natural gad purification" Energy and Enviromental Science, vol. 3, p. 343-451, 2010.
Guang Lu et al., "Imparting functionality to a metal-organic framework by controlled nanoparticle encapsulation" Nature Chemistry, vol. 4, p. 310-316, 2012.
Carolina Avedano et al., "Dramatically Different Counductivity Properties of Metal-Organic Framework Polymorphs of Ti(TCNO): An Unexpected Room-Temperature Crystal-to-Crystal Phase Transition", Angew. Chem. Int. Ed. vol. 50, p. 6543-6547, 2011.

A. Alec Talin et al., "Tunable Electrical Conductivity in Metal-Organic Framework Thin-Film Devices", Science, vol. 343, p. 66-69, 2014.
Deok Yeon Lee et al., "Cu-Based Metal-Organic Frameworks for Photovoltaic Application", American Chemical Society, vol. 118, p. 16328-16334, 2014.
Denise Zacher et al., "Thin films of metal-organic frameworks", Chem. Soc. Rev., vol. 38, p. 1418-1429, 2009.
Spencer R. Ahrenholtz et al., "Solvothermal Preparation of an Electrocatalytic Metaltoporphyrin MOF Thin Fiim and its Redox Hopping Charge-Transfer Mechanism", American Chemical Society, vol. 136, p. 2464-2472, 2014.
Extended European Search Report dated Apr. 12, 2016 issued in corresponding European Patent Application No. 15198499.4.
Tranchemontagne, et al. "Room temperature synthesis of metal-organic frameworks: MOF-5, MOF-74, MOF-177, MOF-199, and IRMOF-0", Tetrahedron, Elsevier Science Publishers, vol. 64, No. 36, pp. 8553-6557 (2008).
Loera-Serna, et al. "Electrochemical behavior of [Cu3(BTC)2] metal-organic framework: The effect of the method of synthesis," Journal of Alloys and Compounds, vol. 540, pp. 113-120 (2012).
Office Action dated Dec. 10, 2019, issued in corresponding Japanese Patent Application No. JP-2015-238765.
Q. Liu et al., 'Facile fabrication and adsorption property of a nano/microporous coordination polymer with controllable size and morphology' *Chem. Commun.* vol. 48, pp. 8814-8816, 2012.

\* cited by examiner

MULTIFUNCTIONAL SUPRAMOLECULAR HYBRIDS ENCOMPASSING HIERARCHICAL SELF-ORDERING OF METAL-ORGANIC FRAMEWORK NANOPARTICLES AND METHOD OF PREPARING SAME

CROSS REFERENCE TO RELATED APPLICATION

This application claims priority to and the benefit of Korean Patent Application No. 10-2014-0174904 filed in the Korean Intellectual Property Office on Dec. 8, 2014, and Japanese Patent Application No. 2015-238765 filed in the Japanese Intellectual Property Office on Dec. 7, 2015, the entire contents of each of which are incorporated herein by reference.

BACKGROUND

1. Field

Example embodiments relate to multifunctional supramolecular hybrids encompassing hierarchical self-ordering metal-organic framework nanoparticles and a method of preparing the same.

2. Description of the Related Art

A metal-organic framework (MOFs) is an inorganic-organic hybrid material having three-dimensionally extended architectures, constructed from repeating symmetric units through self-assembly of molecular building blocks. MOFs or porous coordination polymers (PCPs) may be designed to fabricate various functional crystalline (porous or non-porous) materials by employing multitude of coordinating organic linkers and metal ions, resulting in many chemical and physical characteristics. MOFs include a three-dimensional crystalline nanopore structure having a very large inner surface area of generally greater than about 1000 $m^2/g$.

By virtue of the designable potential of MOFs, researchers could fabricate materials to target applications such as gas separation/storage, a fuel cell, an optical sensor, porous magnetics, stereoisomer separation/catalyst, a photo-catalyst, molecular sieving, etc.

As MOFs are generally obtained as a single-crystal material, the synthesis conditions used affect the resulting physicochemical properties. For instance, literature on MOF materials shows drastic changes in crystalline structures, particle size and mode of coordination (ultimately determines topological feature of the end product) by varying temperature, pressure, solvent, and pH conditions Despite being a single crystalline material, some materials based on MOFs have emerged in the last few years. For example, a polymer blend or quantum dot-doped MOF composite is reported to have improved mechanical and optical characteristics so that it has improved performance of gas separation/storage or catalyst/magnetic/optical usage as a host material.

Recently, MOFs in a thin film form have been explored with electronic applications in mind (US 20140045074 A1). Notably, the MOF material named by Hong Kong University of Science and Technology-1, known also as Cu-BTC or Basolite™ Z300 (BASF trade name), offers a wide range of potential applications due to its easily accessible microporous structure and open copper (Cu) metal sites. In addition, HKUST-1 features a large inner surface area of about 2100 $m^2/g$. Recent studies have demonstrated a number of significant structural properties of HKUST-1 in other avenues (besides gas storage/separation), encompassing proton conduction, electrical conductivity, chemical separation, Li—S battery, electrospun functional textiles, and toxic ion capture, to name just a few examples.

Limiting parameters of existing methods associated with hybrid materials technologies can be summarized as follows:

Conventional methods for synthesizing pure MOF compounds typically require prolonged (few days to 1 week) hydrothermal or solvothermal reactions comprising organic linkers and metal ion solution.

Crucial parameter to determine optical/catalytic/magnetic and other functional properties lies in the particle size of MOF material. However, state-of-the-art hydrothermal reactions do not allow precise control over exact MOF particle size, thereby producing a larger distribution of micron-sized particles instead.

Manufacturing MOFs in the form of thin films involves the use of costlier self-assembled monolayers (SAMs), this strategy also does not allow fabrication over large surface areas.

The majority of MOF materials are undesirable electrical conductors. Two important aspects, namely MOF grain boundaries and localized charge in the framework (undesirable electron delocalization) are reasons for relatively weak charge transport in MOFs, resulting in a semiconductor or an insulator.

Although the demonstration of plausible charge mobility from metal centres in HKUST-1 with the help of extrinsic electron-rich guest (e.g. Tetracyanoquinodimethane (TCNQ) is promising in turning MOFs into electrical conductors, the measured electrical conductivity decreases rapidly when the distance between two electrodes (deposited on HKUST-1 thin film) increases beyond a relatively short gap distance of 100 µm. This presents a limitation for MOF thin films to be utilized in a wide range of practical applications.

SUMMARY

Example embodiments provide a supramolecular metal-organic framework (MOF) material having tunable physical and chemical characteristics.

Example embodiments also provide a method of preparing the supramolecular metal-organic framework (MOF) material.

Example embodiments also provide a molded article including the supramolecular metal-organic framework (MOF) material.

Example embodiments also provide an electronic device including the molded article.

According to example embodiments, a supramolecular metal-organic framework (MOF) material includes a reaction product of a copper compound, a trialkylamine represented by Chemical Formula 1, and a benzene substituted with 3 or more carboxyl groups.

[Chemical Formula 1]

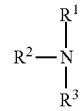

In Chemical Formula 1, each of $R^1$, $R^2$, and $R^3$ are the same or different and are independently a $C_1$ to $C_{10}$ alkyl group.

The copper compound may be copper nitrate ($Cu(NO_3)_2$).

The trialkylamine represented by the Chemical Formula 1 may be triethylamine ($NEt_3$).

The benzene substituted with 3 or more carboxyl groups may be 1,3,5-benzenetricarboxylic acid (BTC).

The reaction product may be obtained in a non-aqueous organic solvent.

The non-aqueous organic solvent may include a $C_1$-$C_{10}$ alkanol, dimethyl sulfoxide (DMSO), N,N-dimethyl formamide (DMF), N,N-diethyl formamide (DEF), N,N-dimethylacetimide (DMAc), acetonitrile (ACN), toluene, dioxane, chlorobenzene, methylethylketone (MEK), pyridine, or a combination thereof.

The supramolecular metal-organic framework material may be in a sol state.

The supramolecular metal-organic framework material may be in a gel state.

The supramolecular metal-organic framework material may be a viscoelastic material.

The supramolecular metal-organic framework material may have a nanoparticle shape.

The supramolecular metal-organic framework material may have a lamella structure.

According to example embodiments, a method of preparing a supramolecular metal-organic framework (MOF) material includes reacting a copper compound, a trialkylamine represented by Chemical Formula 1, and a benzene substituted with 3 or more carboxyl groups in a non-aqueous organic solvent.

The copper compound may be copper nitrate ($Cu(NO_3)_2$).

The trialkylamine represented by the Chemical Formula 1 may be triethylamine ($NEt_3$).

The benzene substituted with 3 or more carboxyl groups may be 1,3,5-benzenetricarboxylic acid (BTC).

The non-aqueous organic solvent may include a $C_1$-$C_{10}$ alkanol, dimethyl sulfoxide (DMSO), N,N-dimethyl formamide (DMF), N,N-diethyl formamide (DEF), N,N-dimethylacetimide (DMAc), acetonitrile (ACN), toluene, dioxane, chlorobenzene, methylethylketone (MEK), pyridine, or a combination thereof.

The non-aqueous organic solvent may be methanol, ethanol, dimethyl sulfoxide (DMSO), N,N-dimethyl formamide (DMF), acetonitrile (ACN) and a mixture thereof.

The supramolecular metal-organic framework material may be in a sol state, and the method of preparing the supramolecular metal-organic framework material may include reacting a solution including the copper compound with a solution including the trialkylamine represented by the Chemical Formula 1 and the benzene substituted with 3 or more carboxyl groups.

The supramolecular metal-organic framework material may be in a gel state, and the method of preparing the supramolecular metal-organic framework material may include reacting a solution including the copper compound with a solution including the trialkylamine represented by Chemical Formula 1 and the benzene substituted with 3 or more carboxyl groups to produce a resultant material, and one of heat-treating the resultant material and allowing the resultant material to stand.

The method of preparing the supramolecular metal-organic framework material may include reacting a solution including the copper compound with a solution including the trialkylamine represented by the Chemical Formula 1 and the benzene substituted with 3 or more carboxyl groups to produce a first resultant material, one of heat-treating the first resultant material and allowing the first resultant material to stand to produce a second resultant material in a gel state, and allowing the second resultant material in the gel state to stand to produce a viscoelastic supramolecular metal-organic framework material.

The method of preparing the supramolecular metal-organic framework material may include reacting a solution including the copper compound with a solution including the trialkylamine represented by the Chemical Formula 1 and the benzene substituted with 3 or more carboxyl groups to produce a first resultant material, one of heat-treating the first resultant material and allowing the first resultant material to stand to produce a second resultant material in a gel state, allowing the second resultant material in the gel state to stand to produce a viscoelastic supramolecular metal-organic framework material, and drying the viscoelastic supramolecular metal-organic framework material to produce a supramolecular metal-organic framework material having a nanoparticle shape.

According to example embodiments, a molded article includes the supramolecular metal-organic framework (MOF) material of example embodiments.

The molded article may have a film shape.

According to example embodiments, an electronic device includes the molded article of example embodiments.

DETAILED DESCRIPTION

Figure 1:
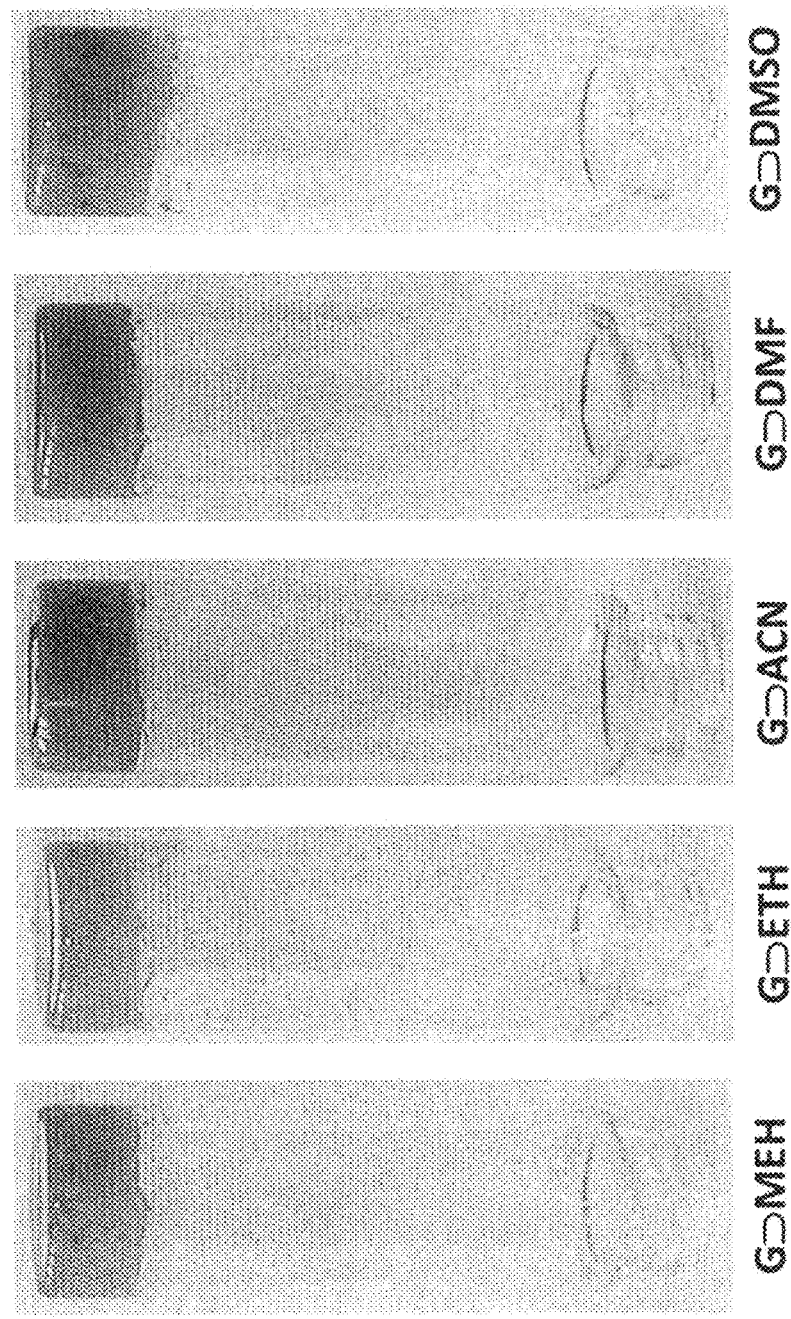
FIG. 1 shows photographs of supramolecular MOF hybrid gels (MOG) obtained from a Cu and BTC system using different organic solvents, wherein G refers to gel, ACN refers to acetonitrile, DMF refers to N,N-dimethyl formamide, DMSO refers to dimethyl sulfoxide, ETH refers to ethanol, and MEH refers to methanol.

The inventive concepts will be described more fully hereinafter with reference to the accompanying drawings, in which example embodiments are shown. However, this disclosure may be embodied in many different forms and is not construed as limited to the example embodiments set forth herein.

In the drawings, the thickness of layers, films, panels, regions, etc., are exaggerated for clarity.

It will be understood that when an element such as a layer, film, region, or substrate is referred to as being "on" another element, it can be directly on the other element or intervening elements may also be present. In contrast, when an element is referred to as being "directly on" another element, there are no intervening elements present.

It should be understood that, although the terms first, second, third, etc. may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

As used herein, when a definition is not otherwise provided, the term "substituted" refers to one substituted with a substituent selected from a $C_1$ to $C_{30}$ alkyl group, a $C_2$ to $C_{30}$ alkynyl group, a $C_6$ to $C_{30}$ aryl group, a $C_7$ to $C_{30}$ alkylaryl group, a $C_1$ to $C_{30}$ alkoxy group, a $C_1$ to $C_{30}$ heteroalkyl group, a $C_3$ to $C_{30}$ heteroalkylaryl group, a $C_3$ to $C_{30}$ cycloalkyl group, a $C_3$ to $C_{15}$ cycloalkenyl group, a $C_6$ to $C_{30}$ cycloalkynyl group, a $C_2$ to $C_{30}$ heterocycloalkyl group, a halogen (—F, —Cl, —Br, or —I), a hydroxy group (—OH), a nitro group (—$NO_2$), a cyano group (—CN), an amino group (—NRR' wherein R and R' are independently hydrogen or a $C_1$ to $C_6$ alkyl group), an azido group (—$N_3$), an amidino group (—C(=NH)$NH_2$), a hydrazino group (—$NHNH_2$), a hydrazono group (=N($NH_2$)), an aldehyde group (—C(=O)H), a carbamoyl group (—C(O)$NH_2$), a thiol group (—SH), an ester group (—C(=O)OR, wherein R is a $C_1$ to $C_6$ alkyl group or a $C_6$ to $C_{12}$ aryl group), a carboxyl group (—COOH) or a salt thereof (—C(=O)OM, wherein M is an organic or inorganic cation), a sulfonic acid group (—$SO_3H$) or a salt thereof (—$SO_3M$, wherein M is an organic or inorganic cation), a phosphoric acid group (—$PO_3H_2$) or a salt thereof (—$PO_3MH$ or —$PO_3M_2$, wherein M is an organic or inorganic cation), and a combination thereof, instead of hydrogen of a compound or group.

As used herein, when a definition is not otherwise provided, the term "hetero" refers to one including 1 to 3 heteroatoms selected from N, O, S, Si, and P.

As used herein, the term "alkylene group" refers to a linear or branched saturated aliphatic hydrocarbon group having a valence of 2 or more and optionally including at least one substituent. As used herein, the term "arylene group" refers to a functional group optionally including at least one substituent and having a valence of 2 or more formed from removal of at least two hydrogens in at least one aromatic ring.

In addition, the term "aliphatic organic group" refers to a $C_1$ to $C_{30}$ linear or branched alkyl group, the term "aromatic organic group" refers to a $C_6$ to $C_{30}$ aryl group or a $C_2$ to $C_{30}$ heteroaryl group, and the term "alicyclic organic group" refers to a $C_3$ to $C_{30}$ cycloalkyl group, a $C_3$ to $C_{30}$ cycloalkenyl group, and a $C_3$ to $C_{30}$ cycloalkynyl group. Further, the term "carbon-carbon unsaturated bond-containing substituent" refers to a $C_2$ to $C_{20}$ alkenyl group including at least one carbon-carbon double bond, a $C_2$ to $C_{20}$ alkynyl group including at least one carbon-carbon triple bond, a $C_4$ to $C_{20}$ cycloalkenyl group including at least one carbon-carbon double bond in the ring, or a $C_4$ to $C_{20}$ cycloalkynyl group including at least one carbon-carbon triple bond in the ring.

As used herein, the term "combination thereof" refers to a mixture, a stack, a composite, an alloy, a blend, or a reaction product of constituting elements.

According to example embodiments, a supramolecular metal-organic framework (hereinafter referred to as "MOF") hybrid material having the tunable physical or chemical characteristics is provided.

Hereinafter, the supramolecular metal-organic framework (MOF) hybrid material, a method of fabricating the same, and the change of reactivity of the material to various stimuli, a phase change, or a micro-structure and the characteristics are explained in detail with reference to the accompanying drawings.

1. Supramolecular Metal-Organic Framework (MOF) Hybrid Material

The copper-based MOF material, termed HKUST-1 has been investigated in its supramolecular forms enabled by synthesis methods involving different solvents, temperatures, or bases.

The inventors discovered that by combining a high concentration of starting reactants in a small amount of solvent yields previously unreported supramolecular hybrid materials exhibiting remarkable physico-chemical properties.

Particularly, a method according to example embodiments provides a facile formation of supramolecular gel assembly from the reaction among a copper compound, a trialkylamine represented by the following Chemical Formula 1, and benzene substituted with 3 or more carboxyl groups.

[Chemical Formula 1]

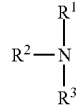

In Chemical Formula 1,

Each of $R^1$, $R^2$, and $R^3$ are the same or different and are independently a $C_1$ to $C_{10}$ alkyl group, for example, a $C_1$ to $C_5$ alkyl group, for example, a $C_1$ to $C_3$ alkyl group.

For example, a method according to example embodiments provides a facile formation of supramolecular gel assembly from the reaction between $Cu(NO_3)_2$ solution and deprotonated 1,3,5-benzenetricarboxylic acid (BTC) using triethylamine base ($NEt_3$).

A reaction performed in a variety of organic solvents resulted in different supramolecular metal-organic gel (MOG) compounds, namely G⊃ACN, G⊃DMF, G⊃DMSO, G⊃ETH and G⊃MEH (where G denotes gel, while the solvents comprise ACN: Acetonitrile, DMF: N,N-Dimethyl Formamide, DMSO: Dimethyl Sulfoxide, ETH: Ethanol, MEH: Methanol, see FIG. 1).

The present inventors found that the use of different solvents for making metal-organic gels could yield unique physical, mechanical and chemical properties with scope for tuneability, which further illustrates structural dependency of multifunctionality.

2. Sol-Gel Transitions

The fabricating the supramolecular metal-organic framework, HKUST-1, has been published, which typically includes reacting 1,3,5-benzenetricarboxylic acid (BTC) with copper (Cu) in a DMSO solvent.

Figure 2:
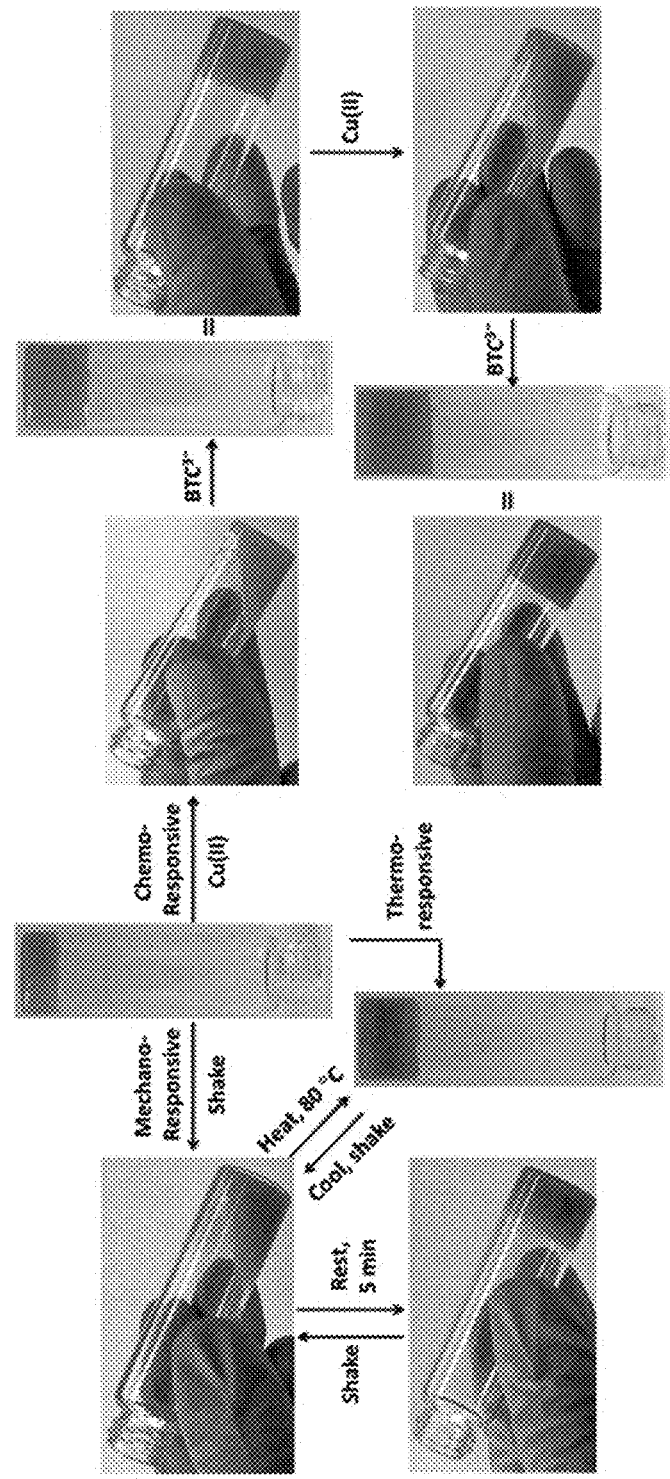
FIG. 2 is a photograph showing multi-stimuli reactive sol-gel converting processes of MOG obtained from DMSO solvent.

However, according to example embodiments, the use of triethylamine base ($NEt_3$) induces unexpected effects whereby molecular self-assembly has resulted in generation of a completely new family of hybrid MOG materials. Detailed study of this gel compound revealed an improved response against thermal, mechanical, and chemical stimuli, as illustrated in FIG. 2.

The unique multi-responsive phenomenon may be described as follows.

Upon MOG formation, subsequent alternate additions of 1 equivalent of BTC and/or 1.5 equivalent of Cu(II) solution cause self-assembly or phase transformation to occur, i.e. switching from gel to sol or vice versa.

In addition to this cationic Cu(II) and anionic $BTC^{3-}$ effects on self-assembly, the application of mechanical forces (by shaking) also disrupts the integrity of the material transforming gel into viscous sol. Surprisingly, when the sol is treated with ultrasonication for about 1 to 2 minutes, or when the sol is allowed to stand for 10 minutes to 15 minutes, it may be recovered to a gel phase. It has been observed that this hybrid material is sensitive to shaking, in which it takes longer time for phase recovery (from sol to gel) to occur when subjected to more intense mechanical forces.

In addition to chemical and mechanical responses, it was found that the gel phase of G⊃DMSO is also achievable by heating the sol for a few minutes, for example, for about 1 to 2 minutes at 80° C.

3. Transformation of Metal-Organic Gels into Viscoelastic Hybrid Materials

Another unique phase change is found in the G⊃ACN gel obtained by using the acetonitrile solvent. That is, it is observed that the gel is transformed into a solid-like material.

Figure 3:
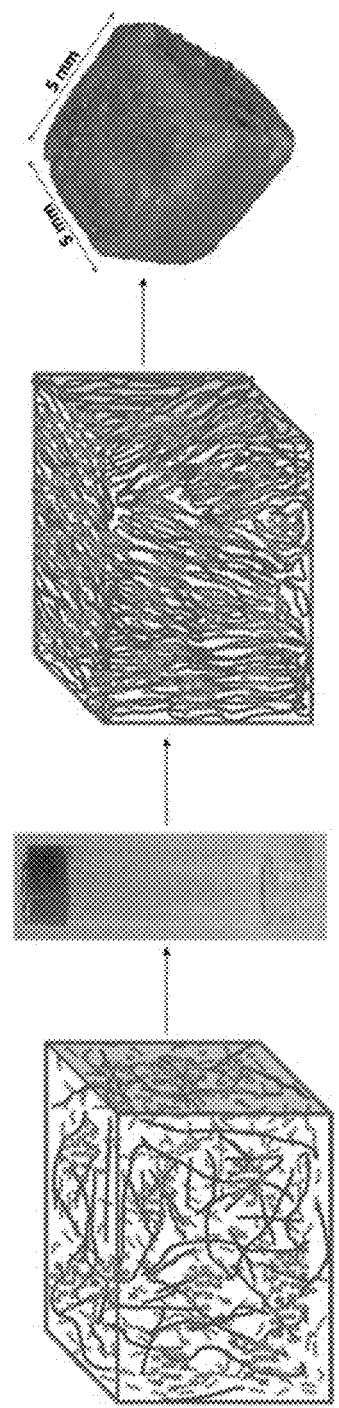
FIG. 3 is a schematic view showing a phase change of MOG obtained from the ACN solvent into a viscoelastic material.

FIG. 3 is a schematic view showing a phase change from the gel to the viscoelastic material.

As shown in FIG. 3, when G⊃ACN is allowed to stand in a closed vial for greater than or equal to about 48 hours, the gel is transformed into the viscoelastic material. One of the important physical properties of the material is its shape persistent capability. The material is soft and stable enough to be cut into any shapes (or deformed using small pressure by hand), or for easy moulding into different 3D shapes, complex features and geometries.

4. Supramolecular Hybrids with Highly Aligned Microstructures

Figure 4:
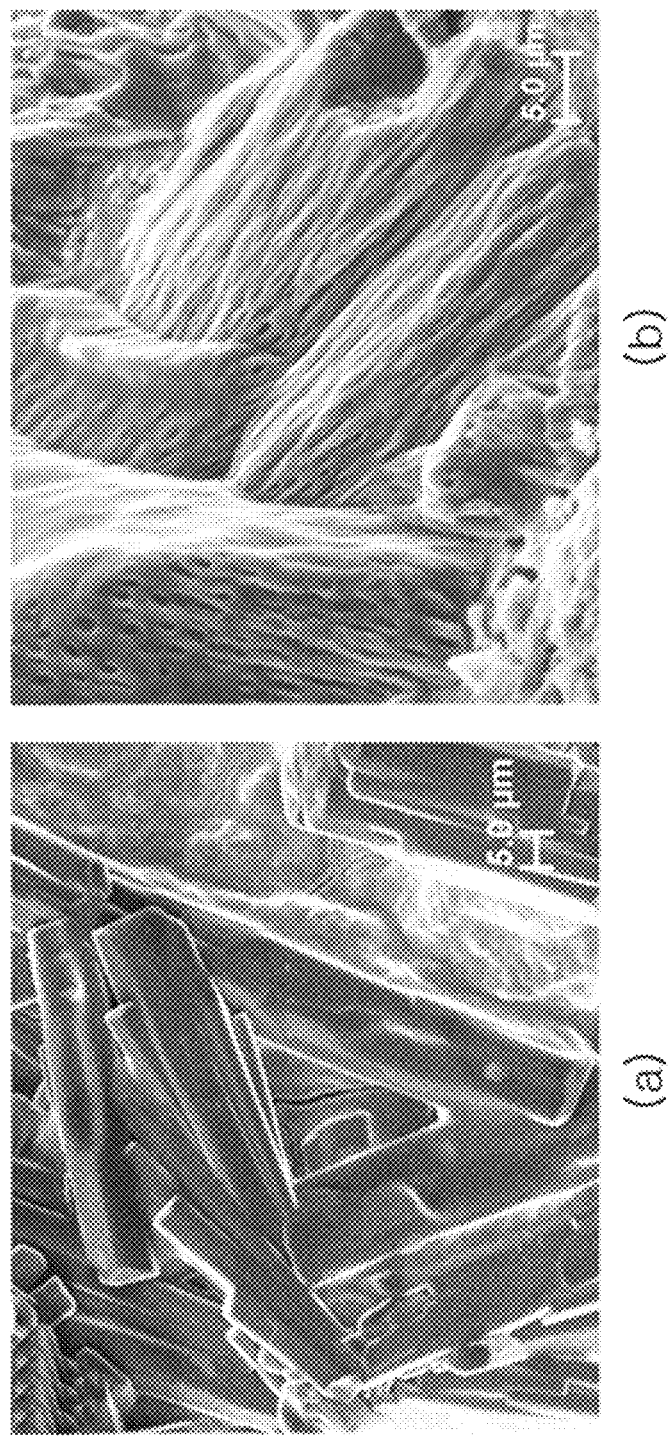
FIG. 4 is SEM images showing MOG (a) obtained from ACN solvent and a viscoelastic material (b) obtained therefrom.
Figure 5:
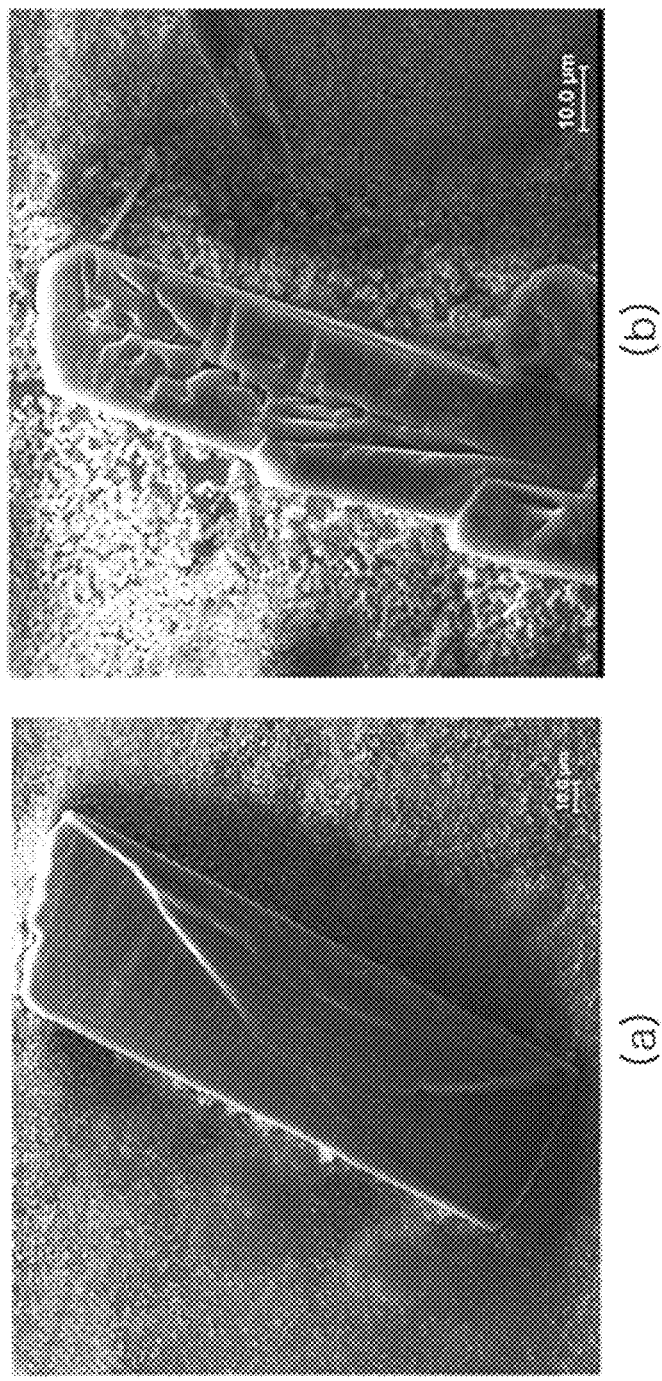
FIG. 5 is SEM images showing MOG obtained from DMSO solvent.
Figure 6:
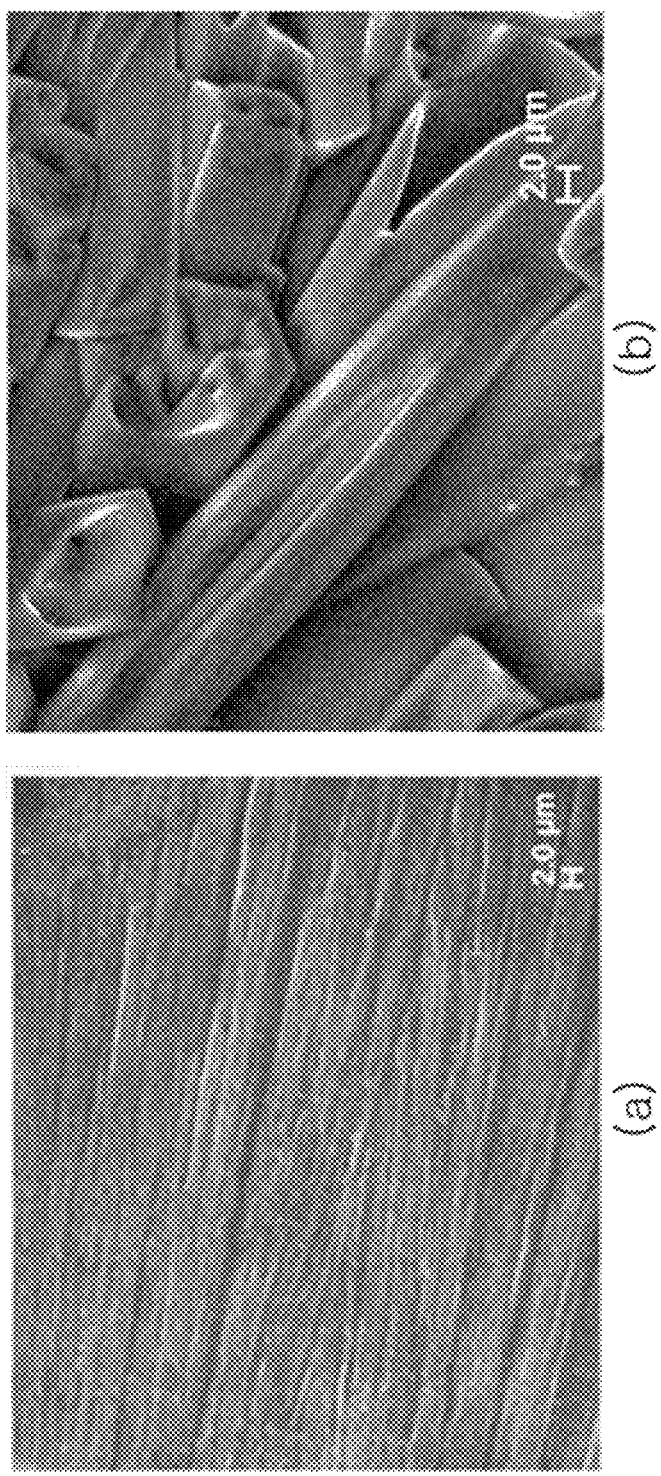
FIG. 6 is SEM images showing MOG obtained from methanol (MEH) solvent.
Figure 7:
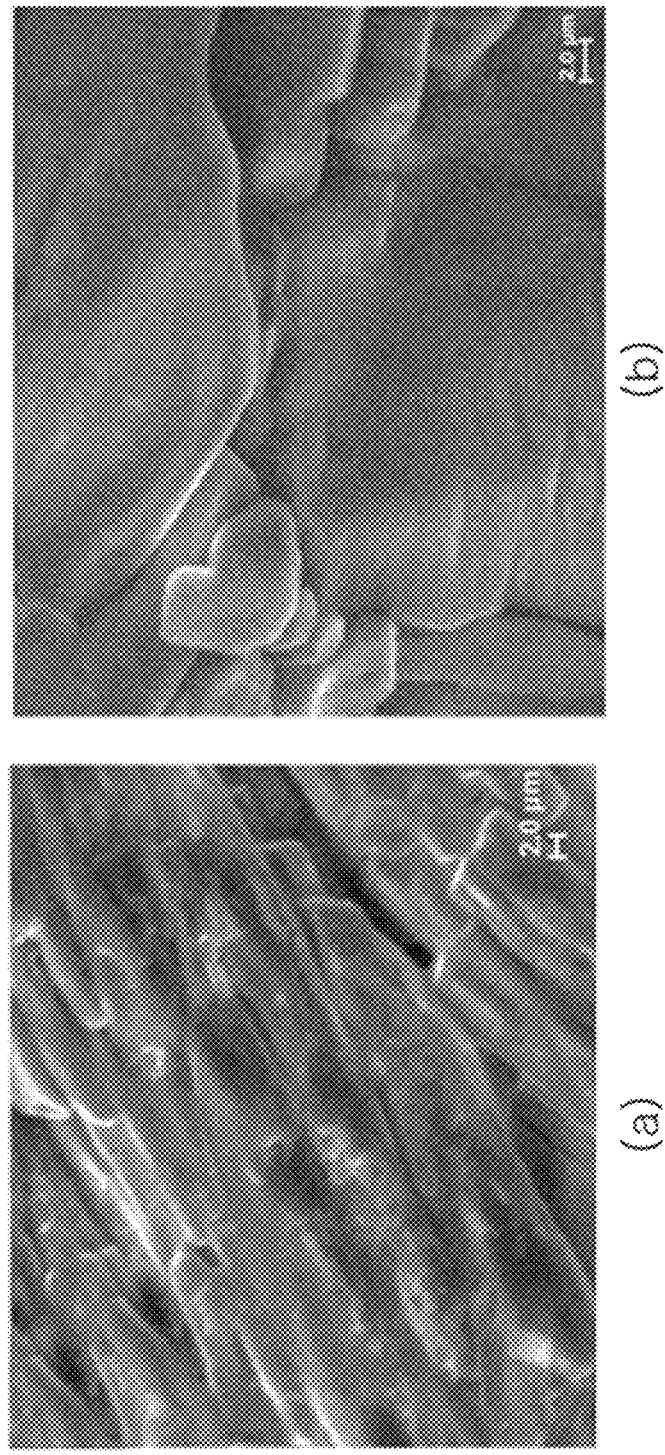
FIG. 7 is SEM images showing MOG obtained from DMF solvent.
Figure 8:
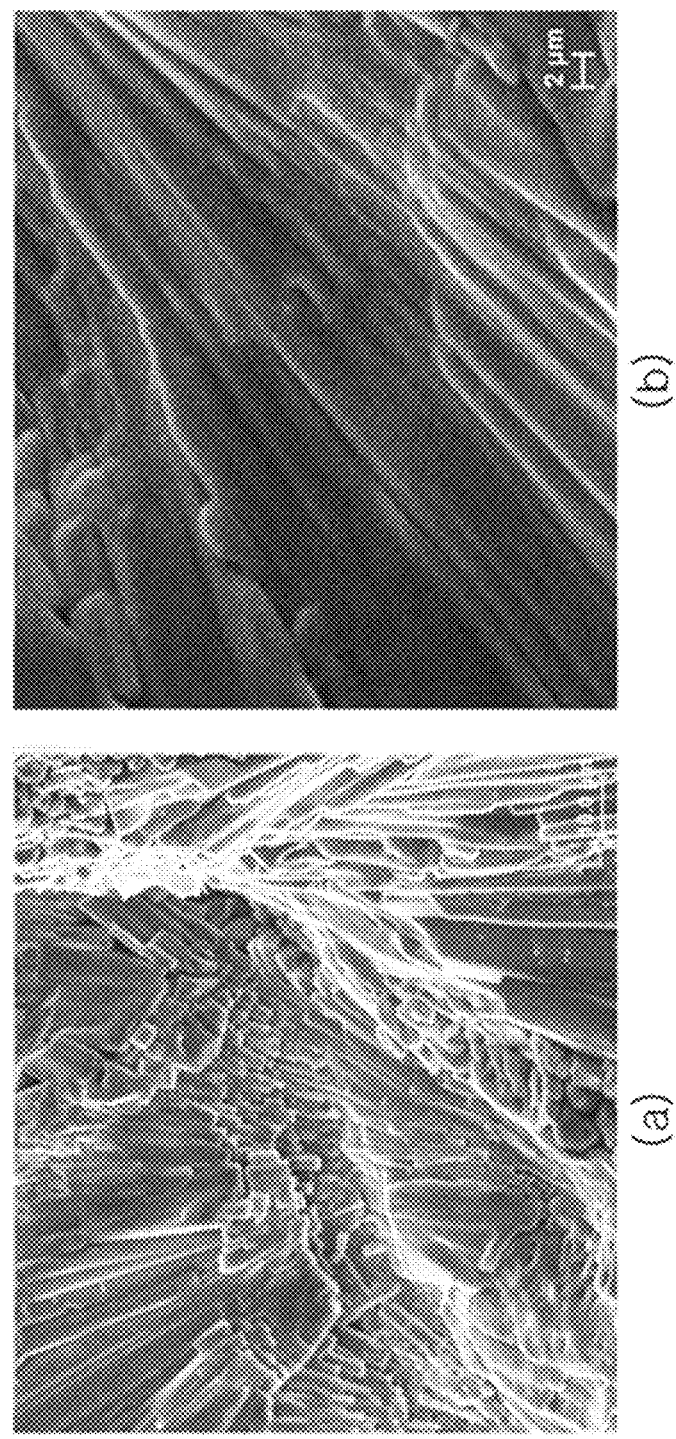
FIG. 8 is SEM images showing MOG obtained from ethanol (ETH) solvent.

FIG. 4 is scanning electron microscope (SEM) photographs of an organic-metal gel (MOG) material (marked (a) in the drawing) obtained using acetonitrile, and a viscoelastic material (marked (b) in the drawing) obtained therefrom.

FIG. 5 to FIG. 8 are scanning electron microscope (SEM) photographs of organic-metal gel (MOG) materials (marked (a) in each drawing) obtained using other solvents, for example, DMSO, methanol, DMF, and ethanol, and gel samples (marked (b) in each drawing) dried therefrom.

As shown in FIG. 5 to FIG. 8, the scanning electron microscope (SEM) photographs of the dried material show that the fiber phase of the material is grown in a predetermined or given direction. In other words, all dried gel samples show thick bundles of fibers growing in the form of strips of various sizes featuring different thicknesses.

Figure 9:
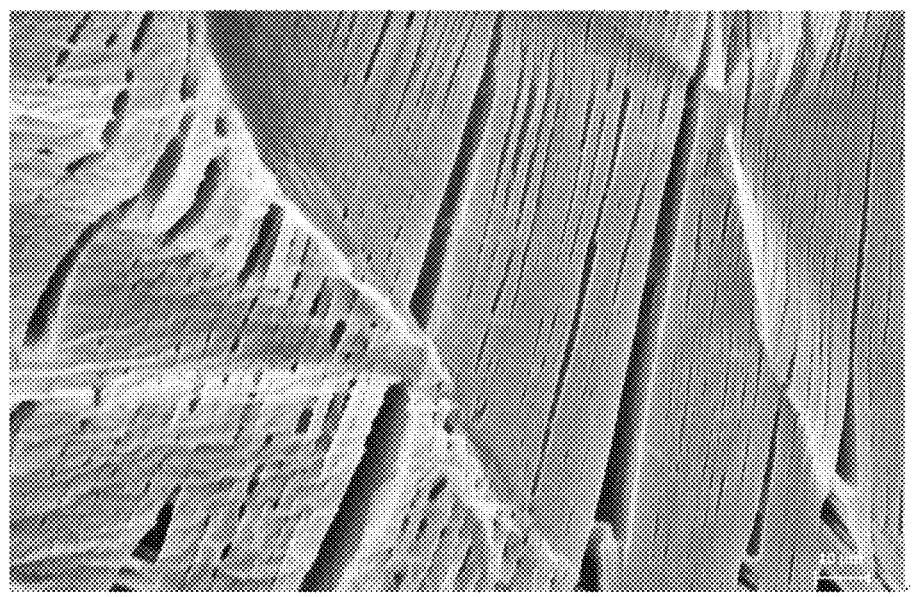
FIG. 9 is a SEM image showing a lamellar structure of MOG obtained in methanol solvent (G⊃MEH) in which one of two reactants is layered on the other one.

FIG. 9 is a SEM image showing a lamellar fibrous network formed in the organic-metal gel (MOG) using a solvent of methanol, G⊃MEH.

5. Supramolecular Hybrids with Tunable Mechanical Properties

Dynamic rheological experiments are performed to study the structural integrity of the supramolecular hybrid MOFs, when subjected to shear deformation (γ) and corresponding shear stress (τ).

The storage modulus (G') and loss modulus (G") are measures of the recoverable elastic response and dissipative viscous behavior, respectively.

The magnitude of the shear modulus (G=τ/γ) is $\sqrt{(G')^2+(G'')^2}$, thereby the shear modulus reflects the material's mechanical rigidity, i.e. its structural resistance (stiffness) against distortion caused by a shear deformation.

When all the gel samples shown in FIG. 4 to FIG. 8 are measured for storage modulus (G') and loss modulus (G") under shear stress according to a frequency sweep dynamic rheological study (Dynamic Mechanical Analysis, DMA), the results are different values, which suggests provision of the hybrid materials with the tunable mechanical properties by using different solvents.

Figure 10A:
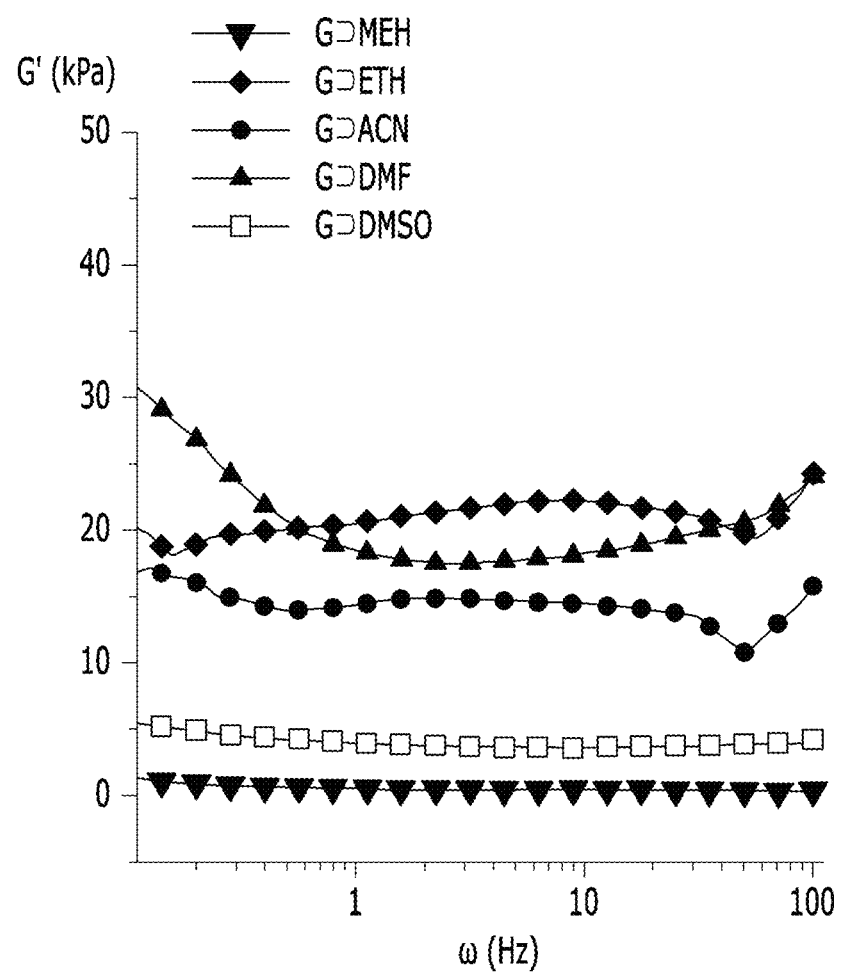
FIG. 10A shows graphs of storage modulus obtained one hour after fabricating the supramolecular MOF hybrid gel (MOG).
Figure 10B:
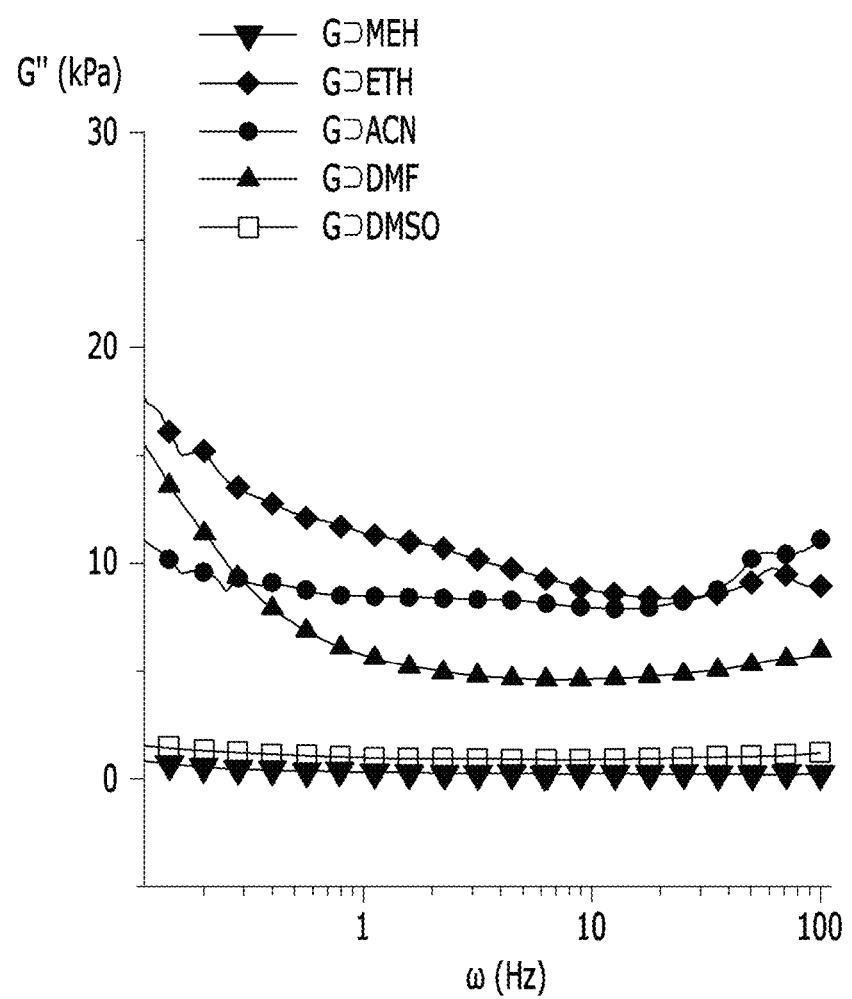
FIG. 10B shows graphs of loss modulus obtained one hour after fabricating the supramolecular MOF hybrid gel (MOG).
Figure 10C:
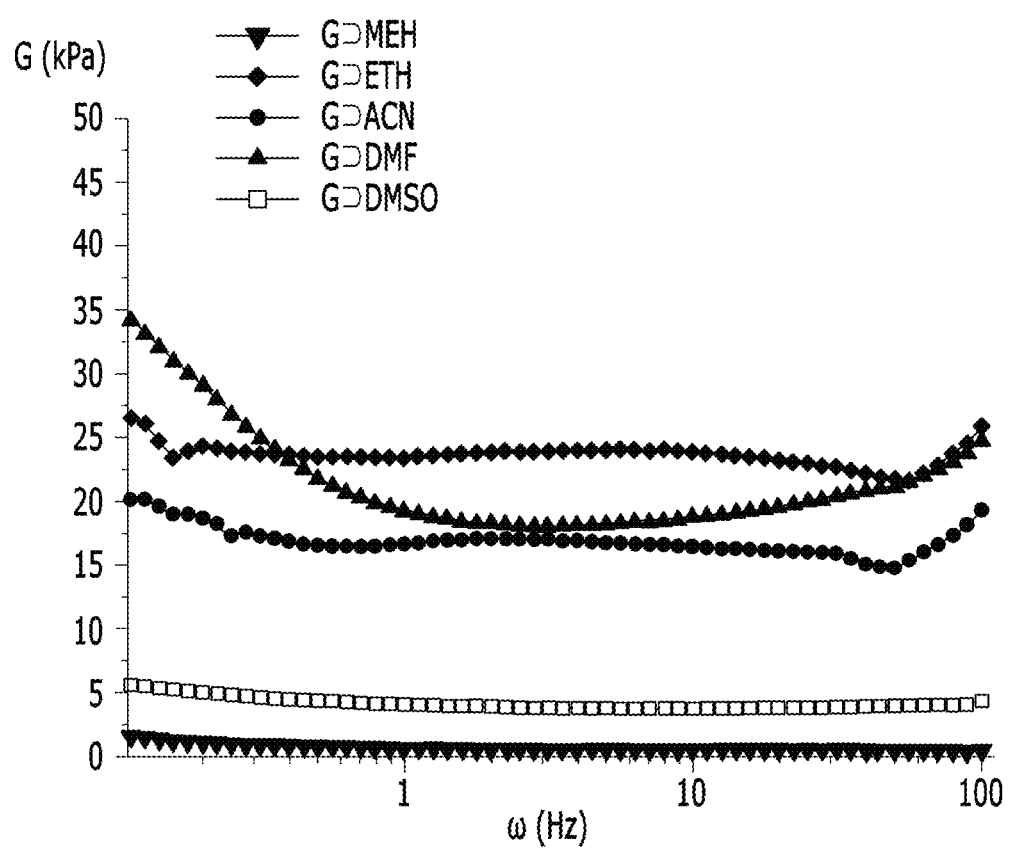
FIG. 10C shows graphs of shear modulus obtained one hour after fabricating the supramolecular MOF hybrid gel (MOG).

FIG. 10A and FIG. 10B show graphs of storage modulus and loss modulus obtained one hour after fabricating the supramolecular MOF hybrid gel (MOG), respectively, and FIG. 10C shows graphs of shear modulus obtained one hour after fabricating the supramolecular MOF hybrid gel (MOG).

Figure 10D:
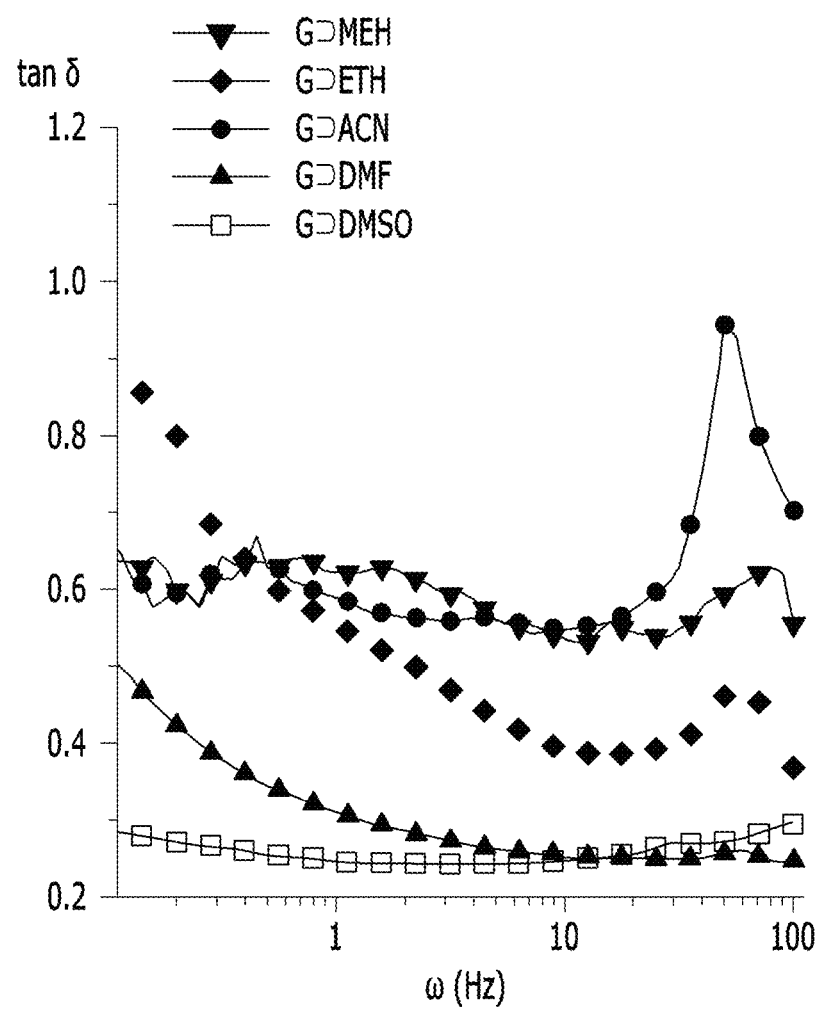
FIG. 10D shows graphs of loss tangent obtained one hour after fabricating the supramolecular MOF hybrid gel (MOG).

Meanwhile, FIG. 10D shows graphs of loss tangent obtained one hour after fabricating the supramolecular MOF hybrid gel (MOG).

According to FIG. 10A and FIG. 10B, G⊃ACN, G⊃DMF, and G⊃ETH have relatively higher storage moduli in the order of about 10 kPa to about 30 kPa, and relatively higher loss moduli in the order of about 5 kPa to about 20 kPa, however, G⊃DMSO and G⊃MEH have significantly lower storage moduli in the order of about 1 kPa to about 5 kPa, and significantly lower loss moduli in the order of about 0.5 kPa to about 1.5 kPa. As a result, G⊃DMSO and G⊃MEH can achieve exceedingly low shear modulus (referring to FIG. 10C).

However, the values of moduli may vary drastically from sample to sample depending on an amount of trapped solvent molecules.

FIG. 10D shows characteristic peaks appearing in G⊃ACN, G⊃MEH and G⊃ETH, corresponding to phase changes associated with relatively higher angular frequencies between about 50 Hz to about 100 Hz. Particularly, a large deviation is observed in G⊃ACN, indicating that its hybrid network is relatively weaker against shear forces imposed at higher frequencies; conversely, G⊃DMSO demonstrates a virtually negligible phase change implying desirable mechanical stability towards shear deformation.

Figure 10E:
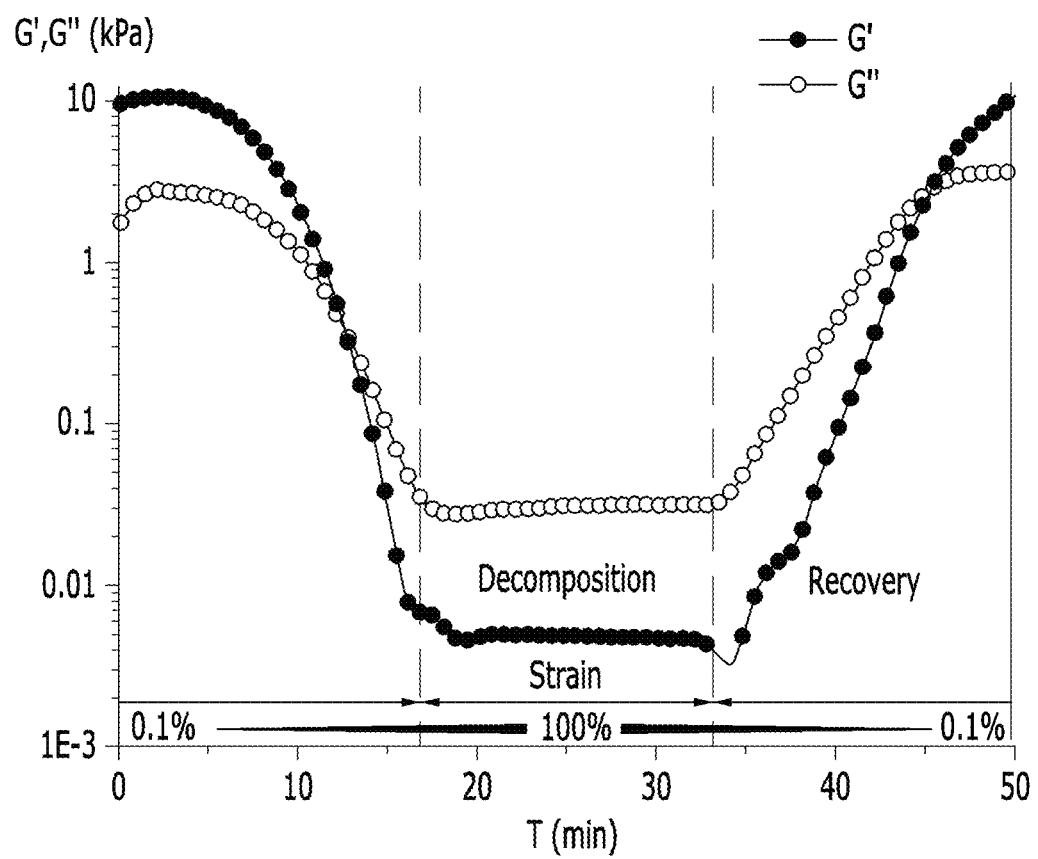
FIG. 10E and FIG. 10F are graphs showing results of dynamic strain sweep measurements on G⊃DMSO, respectively.
Figure 10F:
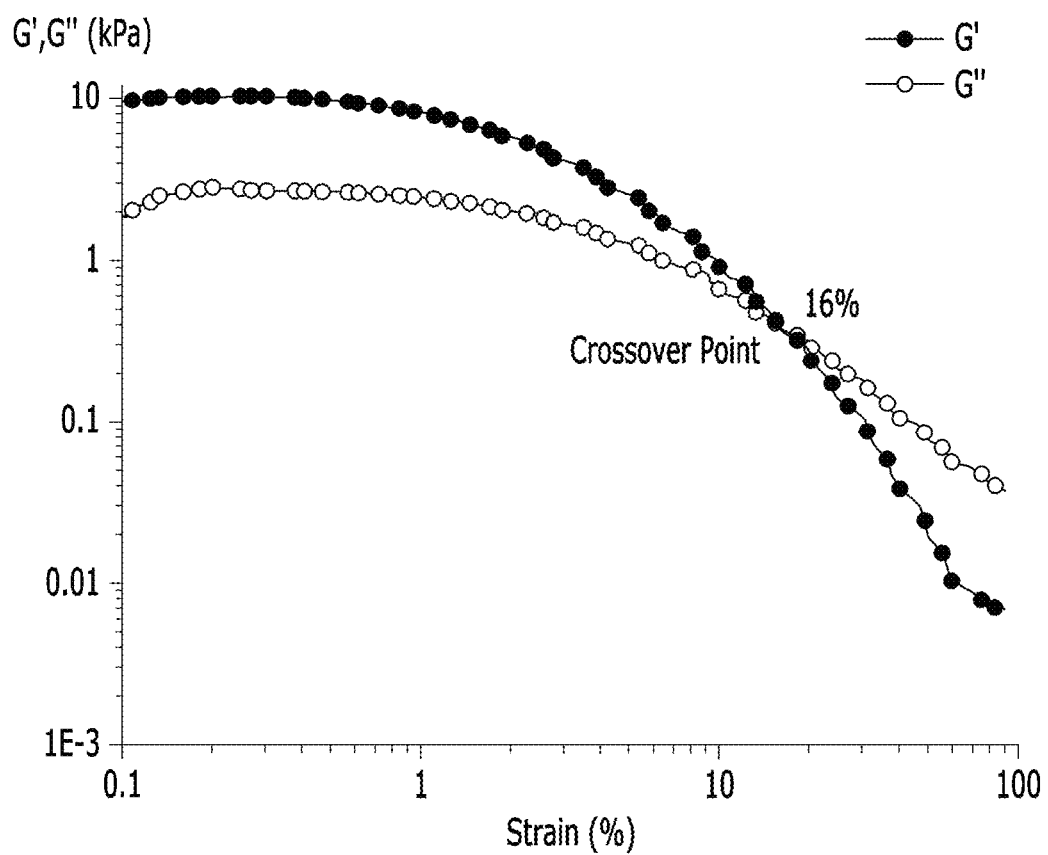

The thixotropic nature of the G⊃DMSO sample is investigated by performing dynamic strain sweep measurements. FIG. 10E and FIG. 10F are graphs showing results of dynamic strain sweep measurements on G⊃DMSO, respectively.

According to FIG. 10E, the G⊃DMSO sample recovers reproducibly to the gel phase within 15 minutes, over the relaxation of strain from 100% to 0.1% at 0.1 Hz angular frequency.

A strain tolerance is determined from the crossover point between a storage moduli (G') and a loss moduli (G") in a dynamic strain sweep measurement.

According to FIG. 10F, the G⊃DMSO sample has a strain tolerance of about 16%.

Meanwhile, the same experiment for all the samples was repeated after 24 hours, 48 hours, and 72 hours to investigate the changes in storage moduli (G') and loss moduli (G") as a function of time.

By monitoring the structural transitions of G⊃ACN via rheology, it is confirmed that how the conversion into subsequent visco-elastic phase (VE⊃ACN) alters overall network rigidity.

Figure 11A:
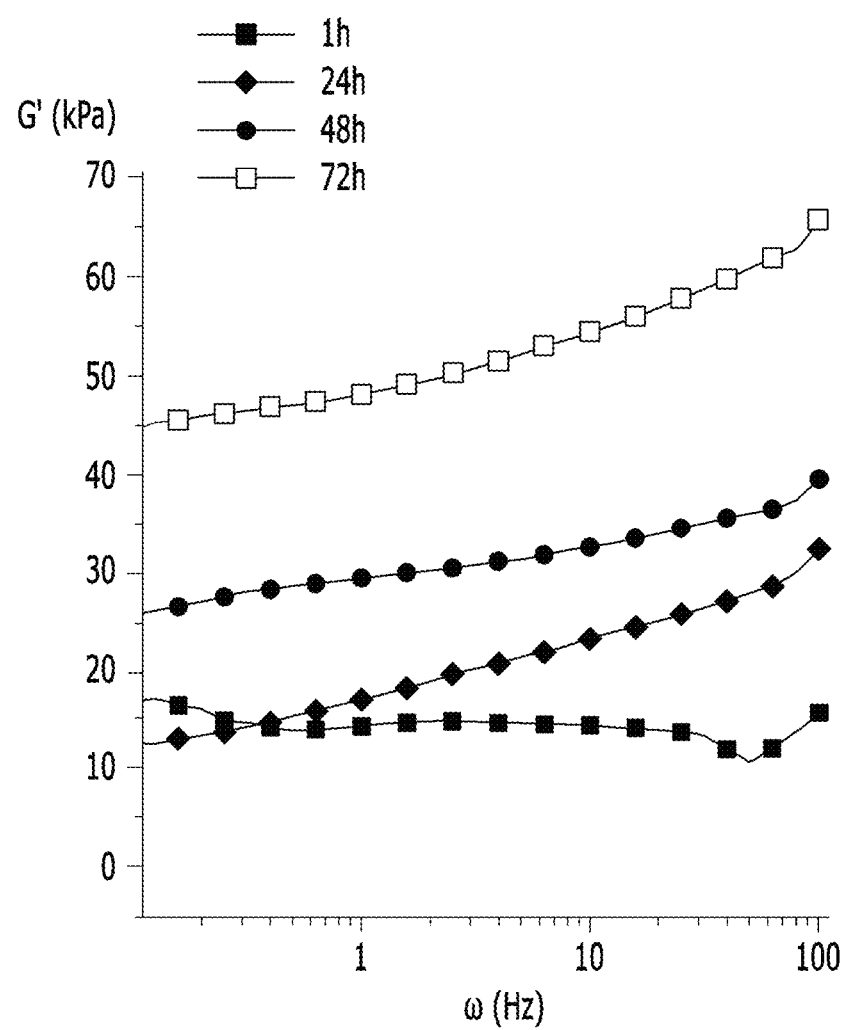
FIG. 11A shows graphs of storage modulus obtained one hour, 24 hours, 48 hours, and 72 hours, after fabricating G⊃ACN.
Figure 11B:
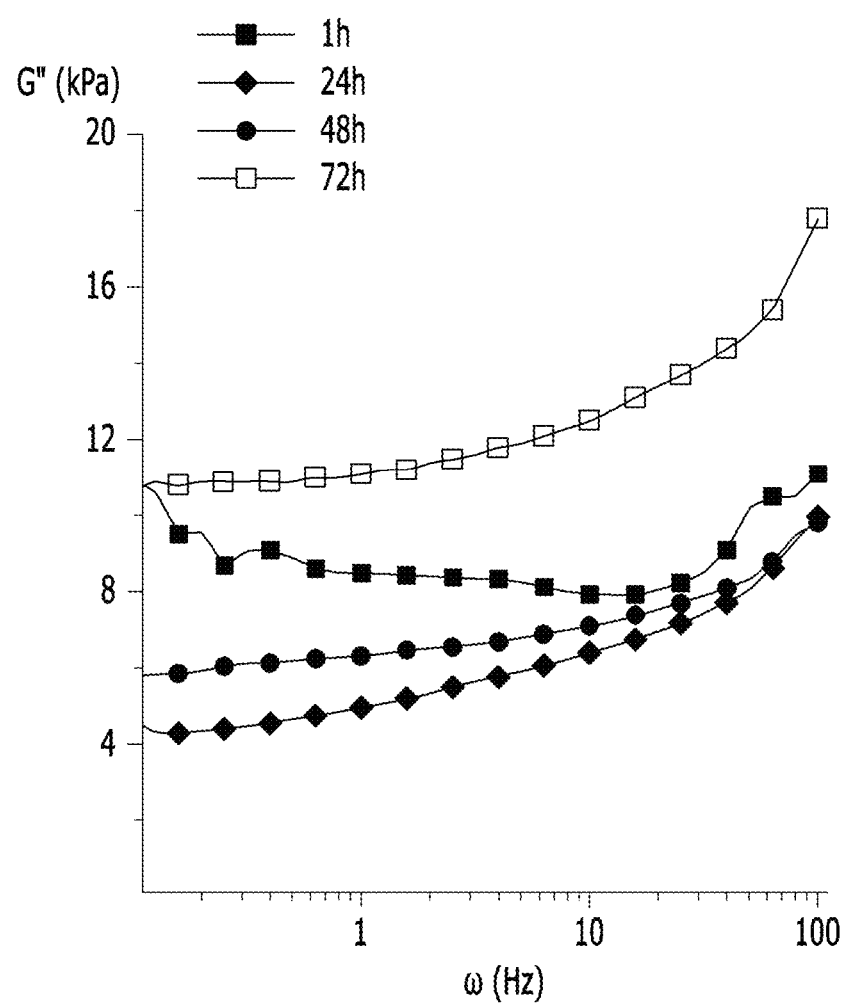
FIG. 11B shows graphs of loss modulus obtained one hour, 24 hours, 48 hours, and 72 hours after fabricating G⊃ACN.
Figure 11C:
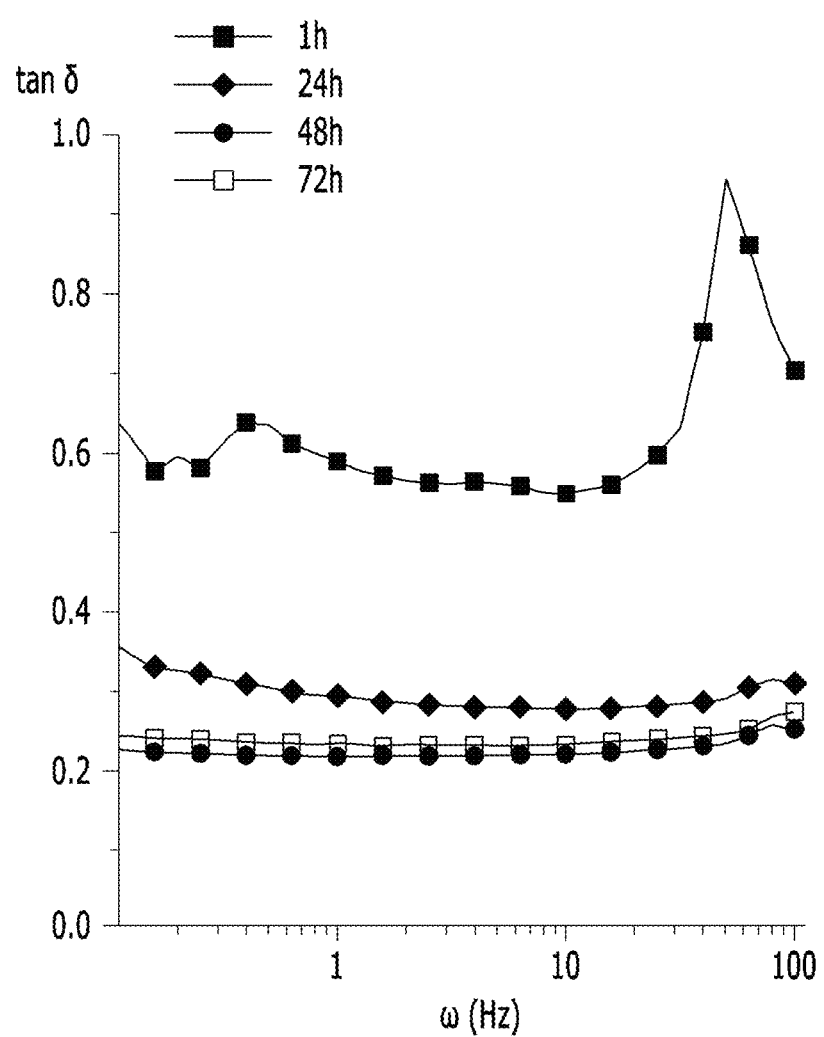
FIG. 11C shows graphs of loss tangent obtained one hour, 24 hours, 48 hours, and 72 hours after fabricating G⊃ACN.

FIG. 11A and FIG. 11B show graphs of storage modulus and loss modulus obtained one hour, 24 hours, 48 hours, and 72 hours, after fabricating G⊃ACN, respectively, and FIG. 11C shows graphs of loss tangent obtained one hour, 24 hours, 48 hours, and 72 hours after fabricating G⊃ACN.

Figure 11D:
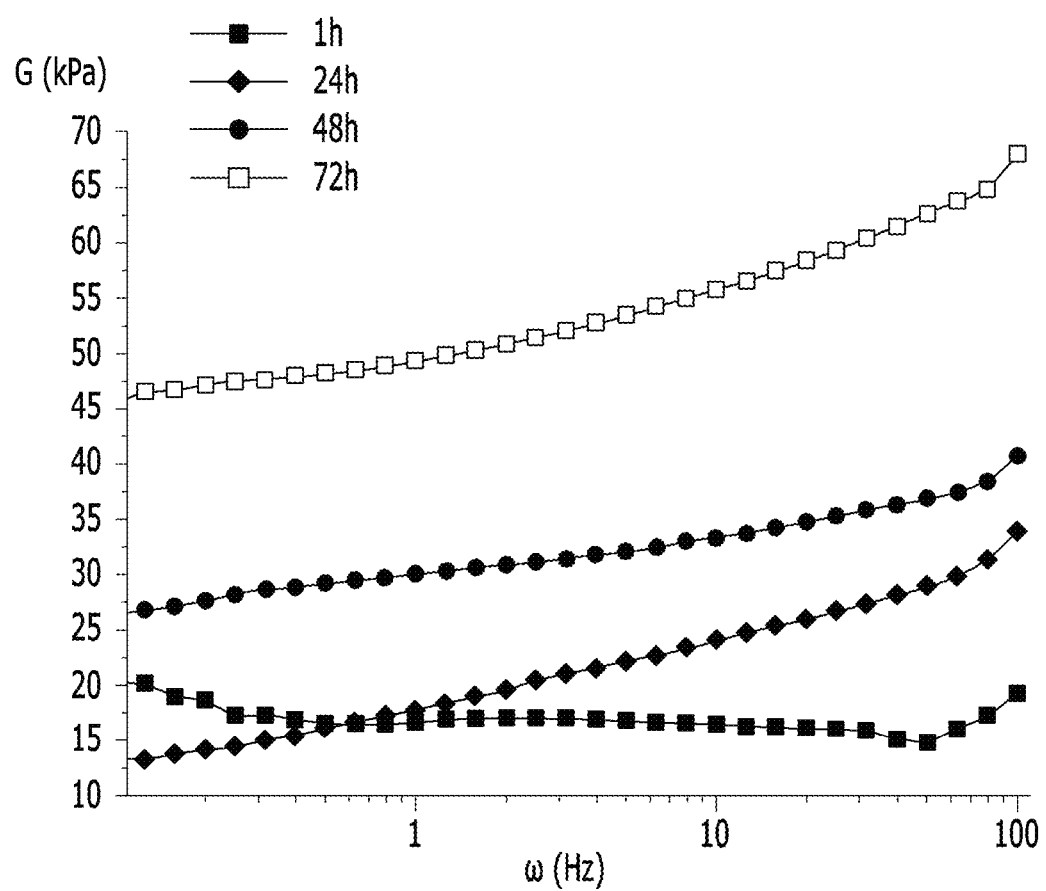
FIG. 11D shows graphs of shear modulus obtained one hour, 24 hours, 48 hours, and 72 hours after fabricating G⊃ACN.

Meanwhile, FIG. 11D shows graphs of shear modulus obtained one hour, 24 hours, 48 hours, and 72 hours after fabricating G⊃ACN.

Dynamic structural variations were evidenced from a substantial rise in storage moduli with time in a non-linear fashion as shown in FIG. 11A and FIG. 11B. For instance, at 0.1 Hz, the magnitude of storage moduli (G') was initially at 17 kPa (1 h), but increased to 26 kPa (48 h) and finally reached 45 kPa (72 h); likewise at higher frequencies, for example at 100 Hz, the magnitude of storage moduli (G') after 72 hours exceeds a factor of three times higher than that of a freshly prepared sample.

FIG. 11C shows that, independent of frequency, there is no phase change detected beyond 48 hours. This finding further substantiates the claim that, over time, relatively weak supramolecular network in G⊃ACN gel becomes more rigid (higher G, referring to FIG. 11D), and thus, is mechanically strengthened against further shear-induced deformation, as it evolves into a viscoelastic material derived from G⊃ACN, constituting a vastly interwoven microstructure (as shown by (b) of FIG. 4).

Figure 11E:
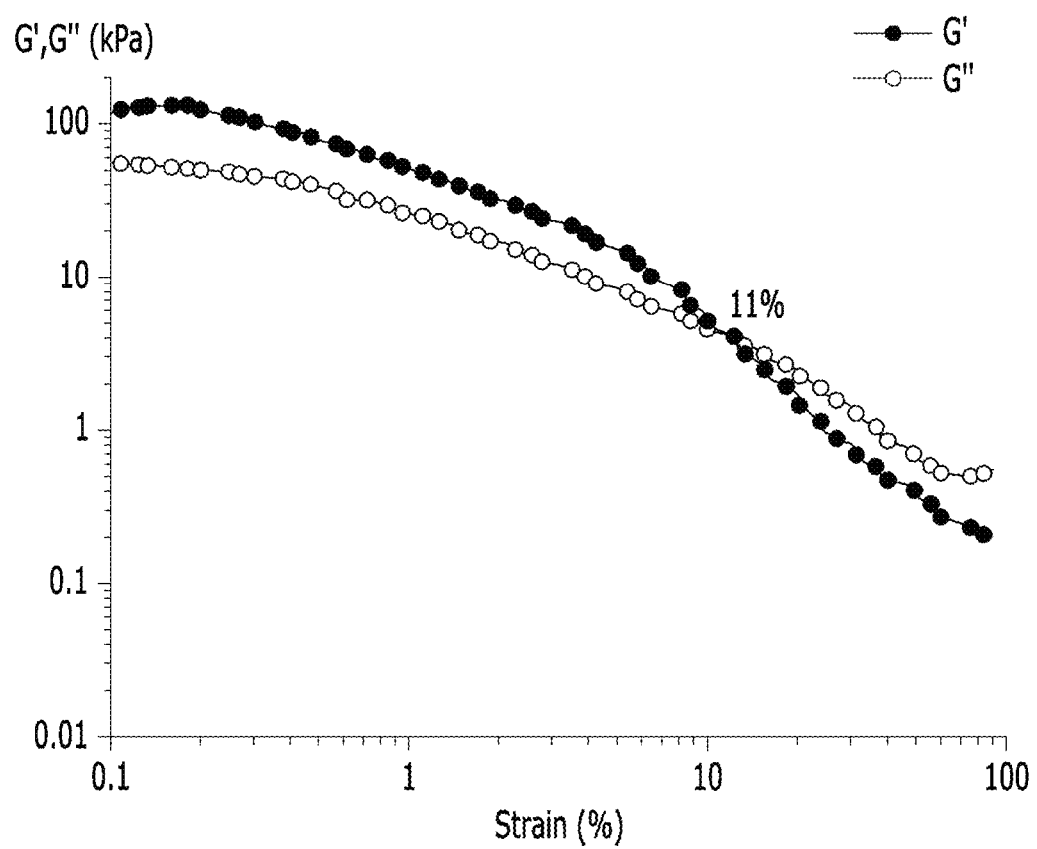
FIG. 11E is a graph showing results of dynamic strain sweep measurements on a viscoelastic material derived from G⊃ACN.

FIG. 11E is a graph showing results of dynamic strain sweep measurements on a viscoelastic material derived from G⊃ACN.

According to FIG. 11E, the viscoelastic material derived from G⊃ACN has a strain tolerance of about 11%

Figure 11F:
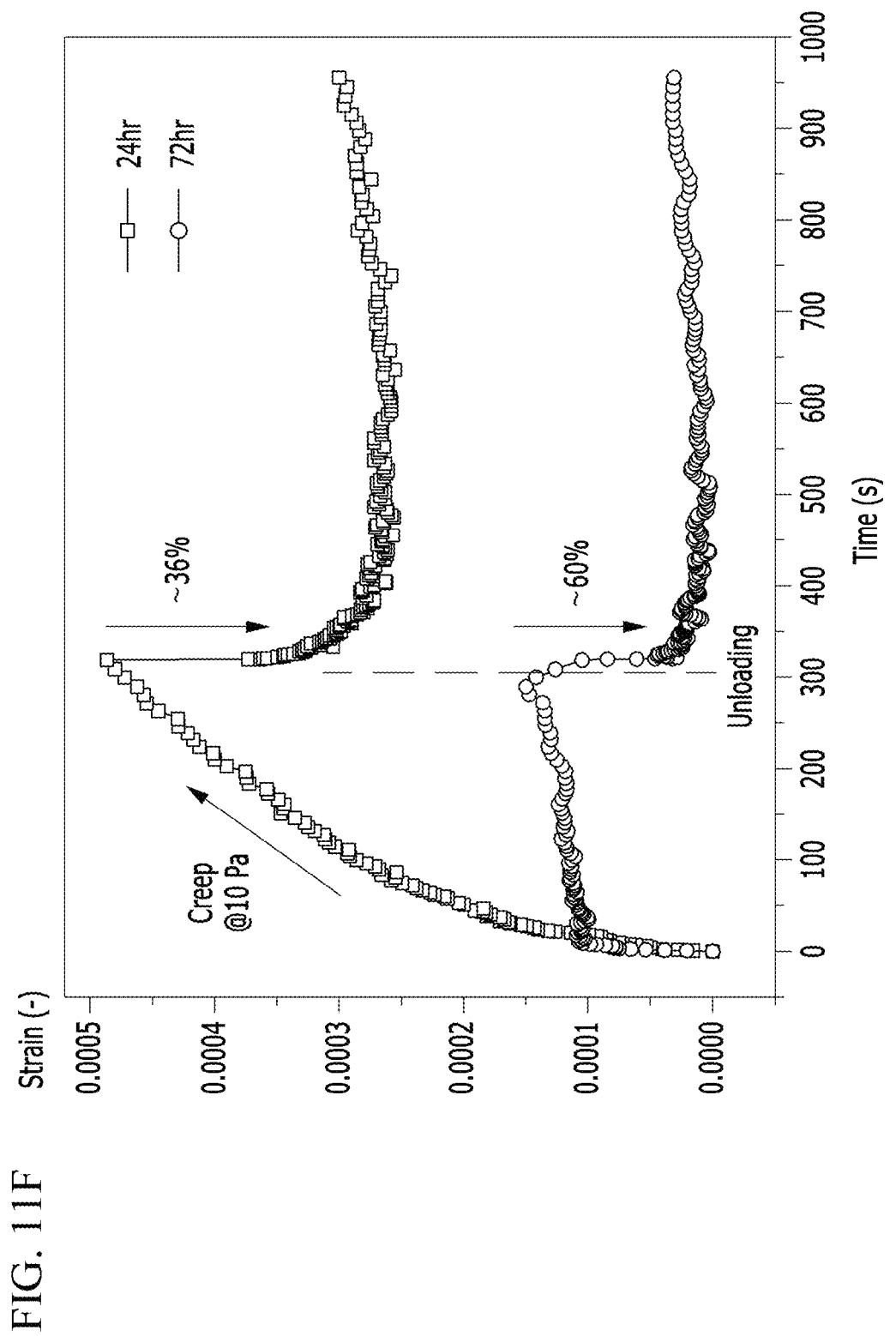
FIG. 11F is a graph showing results of creep recovery tests obtained 24 hours and 72 hours after fabricating G⊃ACN.

Moreover, constant-stress creep experiments are performed in order to compare strain recovery of samples at 24 hours and 72 hours after fabricating the supramolecular MOF hybrid gel (MOG). FIG. 11F is a graph showing results of creep recovery tests obtained 24 hours and 72 hours after fabricating G⊃ACN.

As shown in FIG. 11F, the sample of 72 hours after fabricating G⊃ACN corresponding to a viscoelastic material derived from G⊃ACN shows remarkably higher creep resistance and strain recovery response than the sample of 24 hours after fabricating G⊃ACN.

6. Supramolecular Hybrids with Tunable Electrical Conductivity

Electrical conductivity measurements revealed interesting results from the fact that every sample exhibited different conductivity value, thus suggesting tuneability of electrical properties.

Figure 12A:
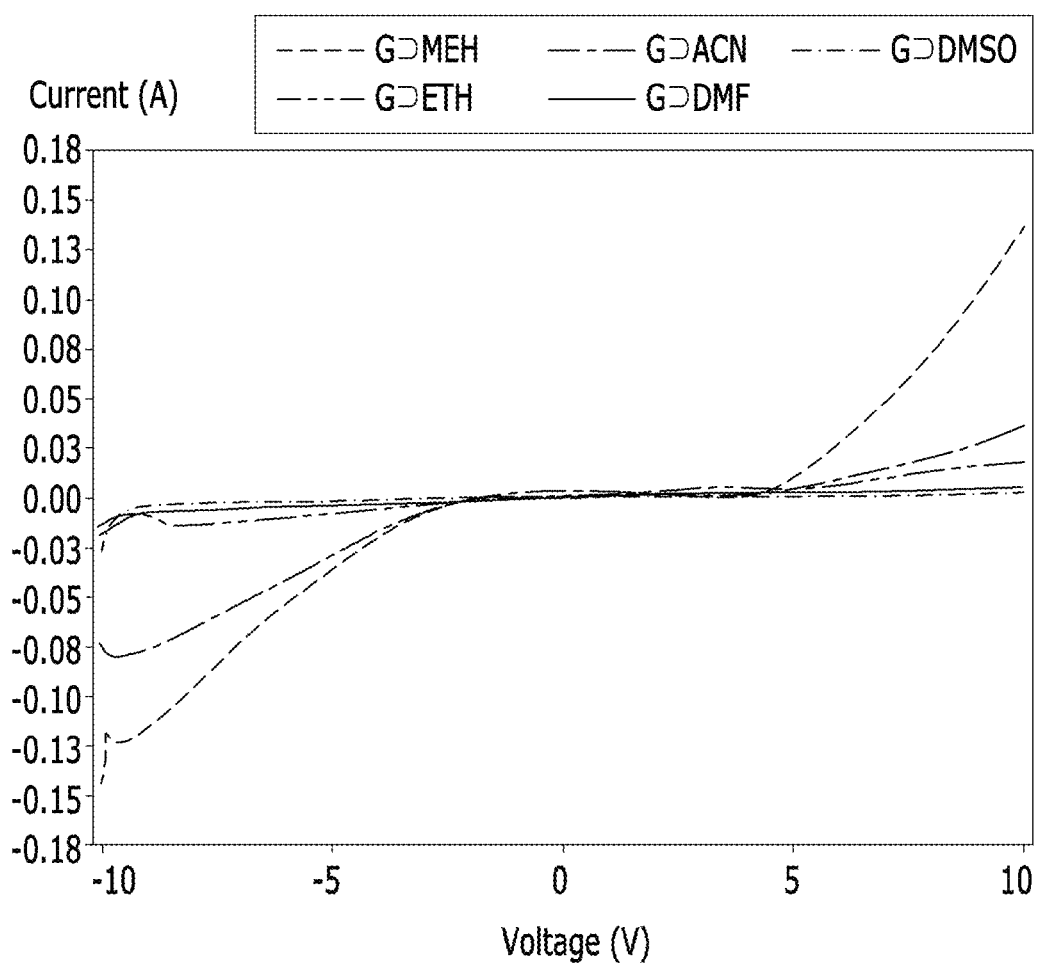
FIG. 12A shows current versus voltage (I-V) graphs of supramolecular MOF hybrid gels (MOG).
Figure 12B:
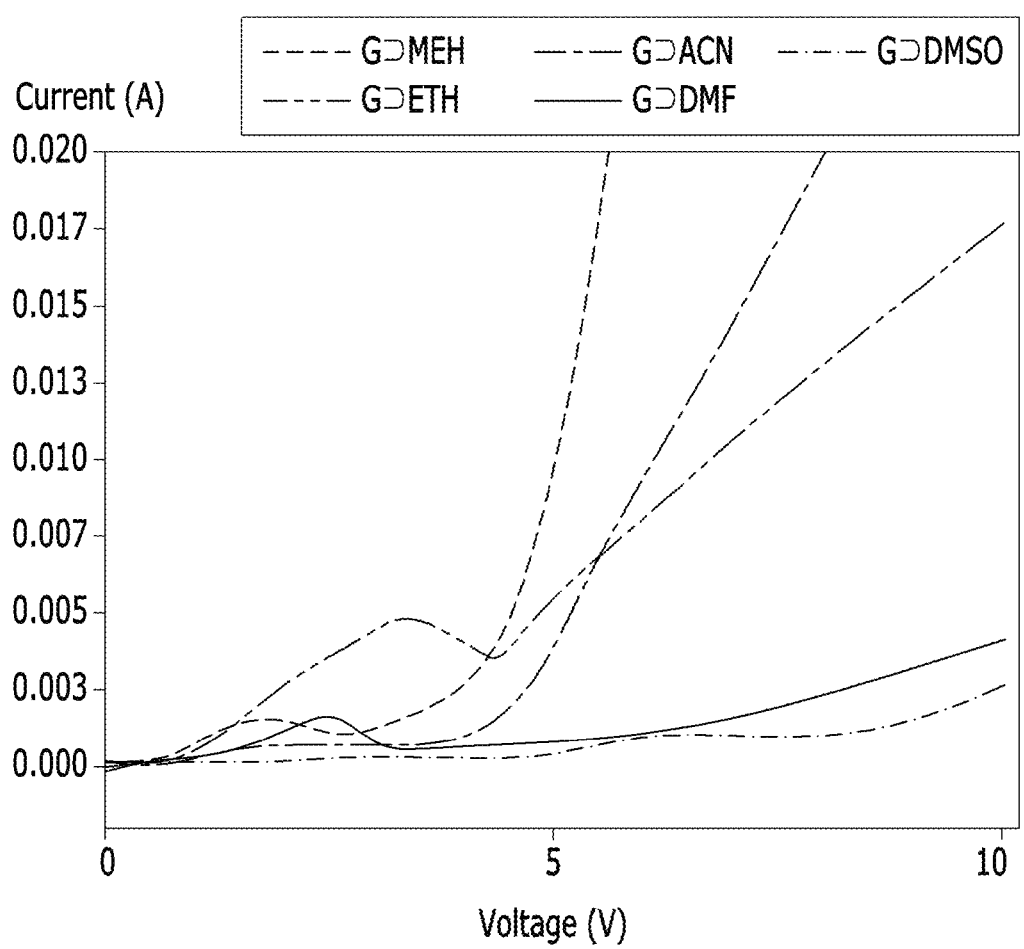
FIG. 12B is a graph enlarging a partial region of FIG. 12A.

Specifically, when measured using a conduction cell including the obtained each organic-metal gel sample and a Keithley 2614B SourceMeter with a 10 V bias, G⊃MEH has the highest electrical conductivity of 9.4402 S/m; on the other hand, G⊃DMSO has the lowest electrical conductivity (0.1388 S/m) (referring to FIGS. 12A and 12B).

FIGS. 12A and 12B show current versus voltage (I-V) graphs of the supramolecular MOF hybrid gel (MOG), wherein FIG. 12B is a graph enlarging a partial region of FIG. 12A.

Relatively lower electrical conductivity in the case of G⊃DMF (0.2255 S/m) and G⊃DMSO could be explained by the "cage effect" of charge carriers (weakly interacting ions), whose mobility is impeded by interacting solvent molecules surrounding the stable gel phase, thus suppressing its overall charge mobility.

The second highest conductivity is observed in G⊃ACN (2.5125 S/m), and the next is in G⊃ETH (1.1367 S/m).

While a relatively low conductivity was ascertained for G⊃ACN (2.5125 S/m), surprisingly, the visco-elastic material (VE⊃ACN) derived from the same gel sample exhibits a markedly higher conductivity at 9.8583 S/m, which translates into an improvement of ~300%. As described in point #3, this material can be cut into different shapes and pressed to mould into thin sheets and membranes, thus its relatively high electrical conductivity value makes the material applicable for potential electronic device applications.

On the other hand, the flat region between ±5 V in FIG. 12A appears to have a relationship with a knee voltage of an aluminum electrode of the Keithley 2614B SourceMeter.

In addition, also from the measurement of AC impedance, it is understood that the organic-metal gels have unique electrical characteristics as a function of frequency.

The typical Warburg impedance having a small hump is observed in all the obtained gel samples. This suggests relatively weakly interacted ionic materials and a relatively strong charge transfer latently generated relative to MOF nanoparticles.

Using Nyquist plots, the results of measuring the ionic conductivity of the samples shows the following.

TABLE 1

| Samples | Ionic conductivity |
|---|---|
| G ⊃ MEH | $4.61 \times 10^{-2}$ S/cm |
| G ⊃ ETH | $1.5 \times 10^{-2}$ S/cm |
| G ⊃ ACN | $1.15 \times 10^{-2}$ S/cm |
| G ⊃ DMF | $8.65 \times 10^{-3}$ S/cm |
| G ⊃ DMSO | $6.92 \times 10^{-3}$ S/cm |
| Viscoelastic hybrid material from G ⊃ ACN | $4 \times 10^{-4}$ S/cm |

Figure 13A:
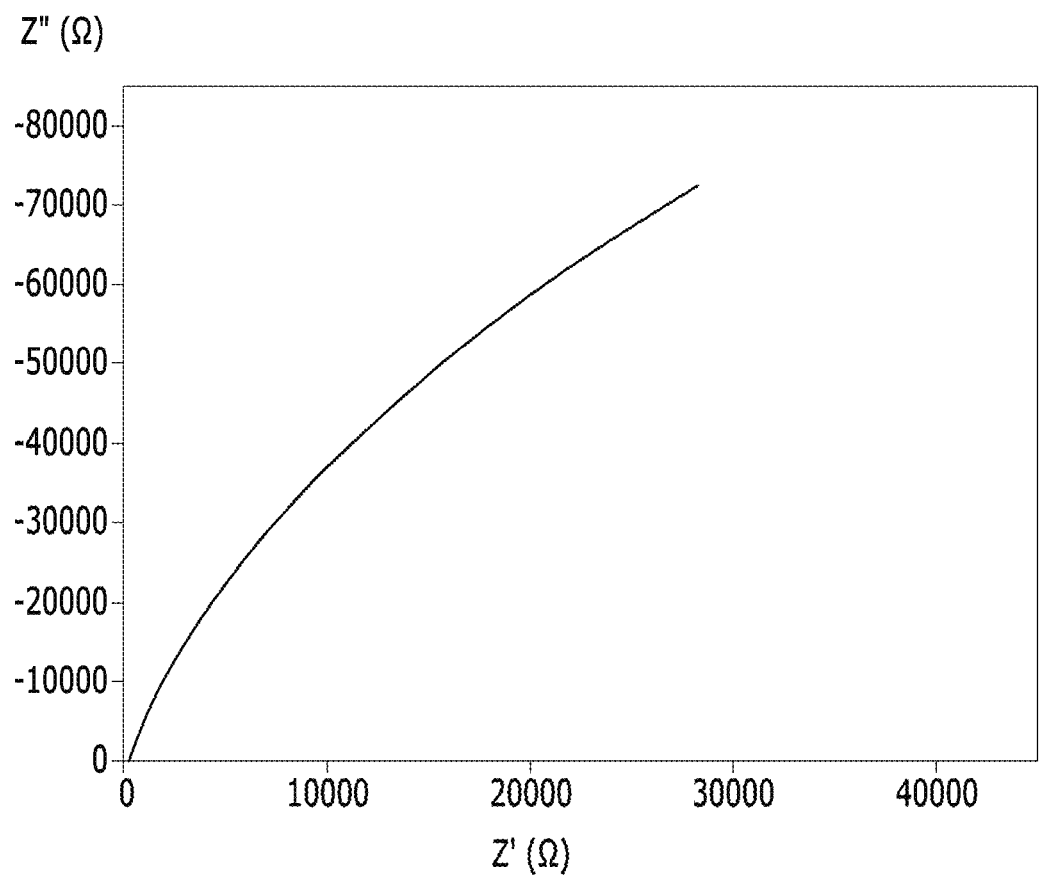
FIG. 13A shows Nyquist plots of G⊃ETH having an extended region in the higher frequency range.
Figure 13B:
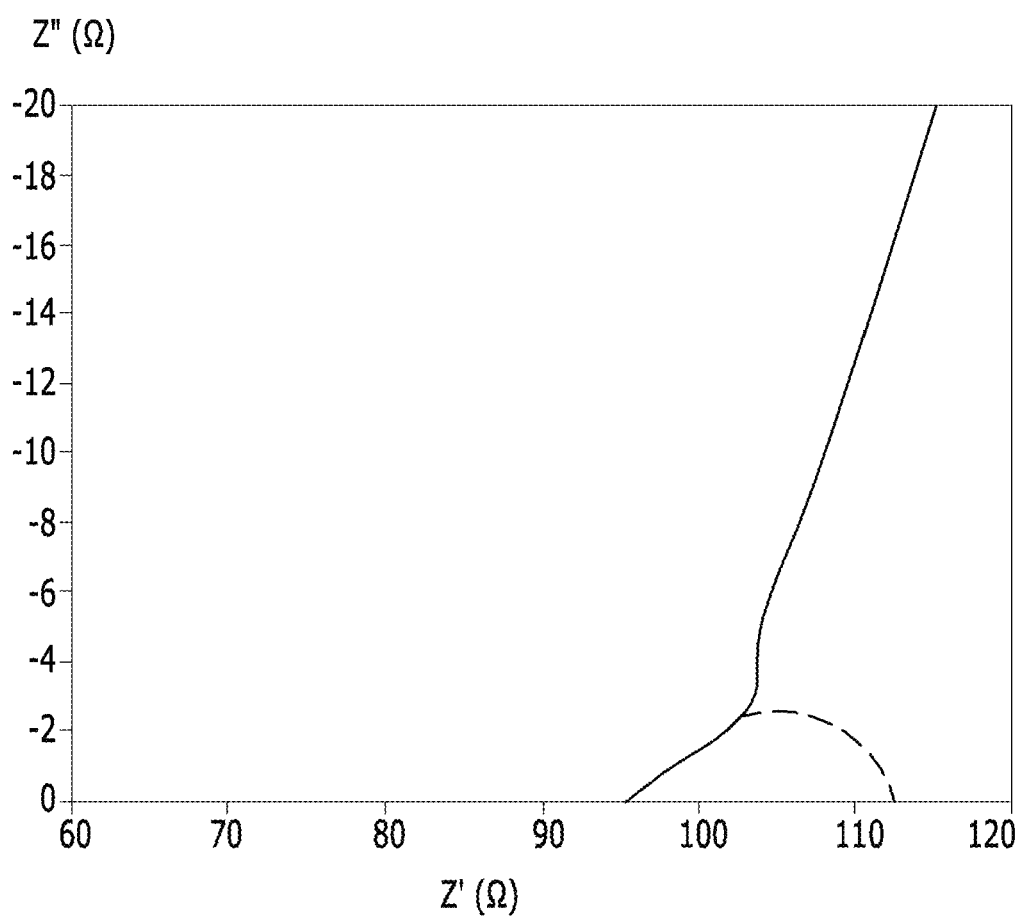
FIG. 13B is a graph enlarging a partial region of FIG. 13A

In addition, FIGS. 13A and 13B show Nyquist plots of G⊃ETH having the extended region at the higher frequency inset, wherein FIG. 13B is a graph enlarging a partial region of FIG. 13A.

Figure 14A:
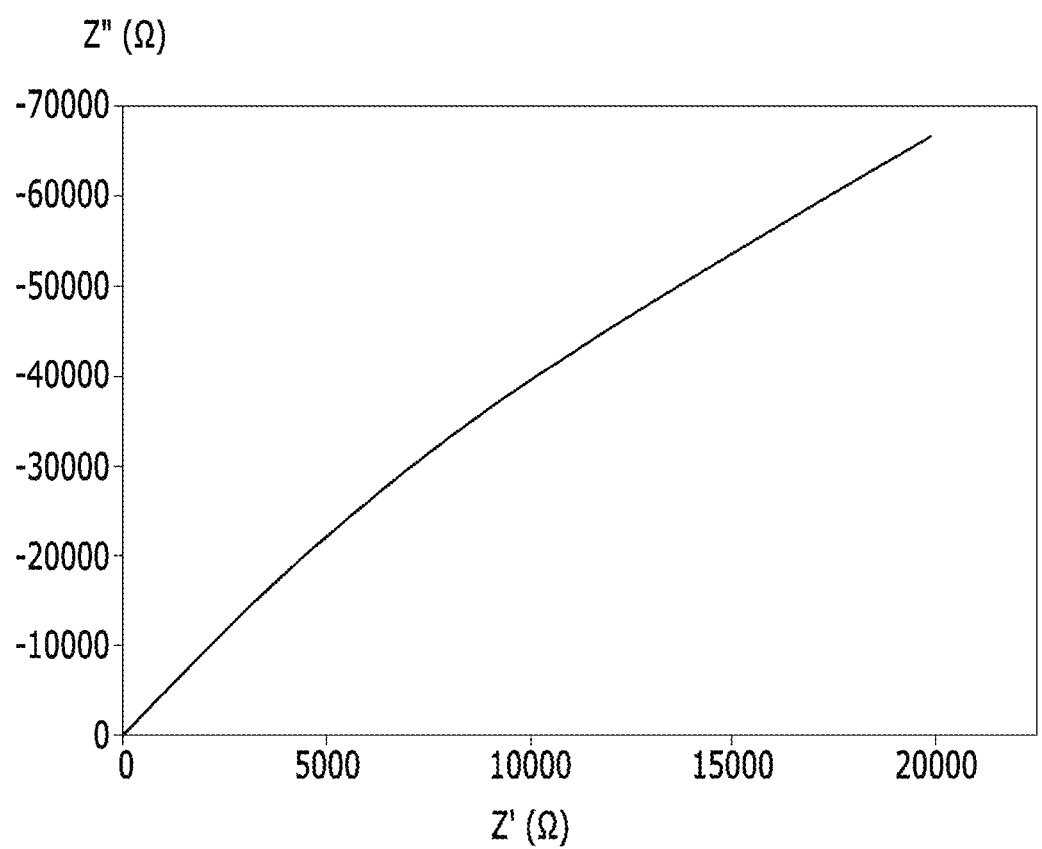
FIG. 14A shows Nyquist plots of the viscoelastic hybrid material induced from G⊃ACN.
Figure 14B:
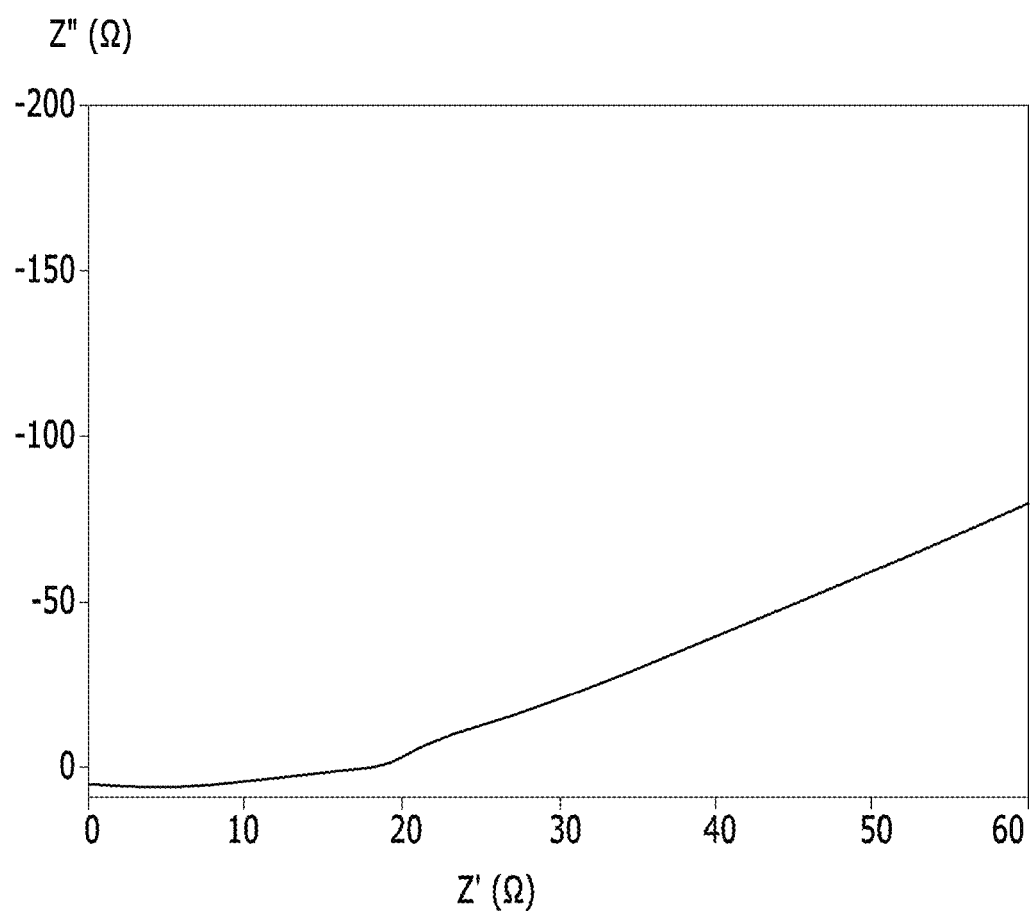
FIG. 14B is a graph enlarging a partial region of FIG. 14A.

FIGS. 14A and 14B show Nyquist plots of a viscoelastic hybrid material induced from G⊃ACN, wherein FIG. 14B is a graph enlarging a partial region of FIG. 14A.

7. Rapid Synthesis Toward Controlled Growth of Hybrid Nanoparticles

The method according to example embodiments for fabricating a supramolecular MOF hybrid material may simultaneously allow control over the emerging supramolecular metal-organic framework hybrid nanoparticles from the gel fibrous assembly.

According to example embodiments, nanoparticles having a particle size of about 30 nm to about 150 nm may be prepared.

Figure 20:
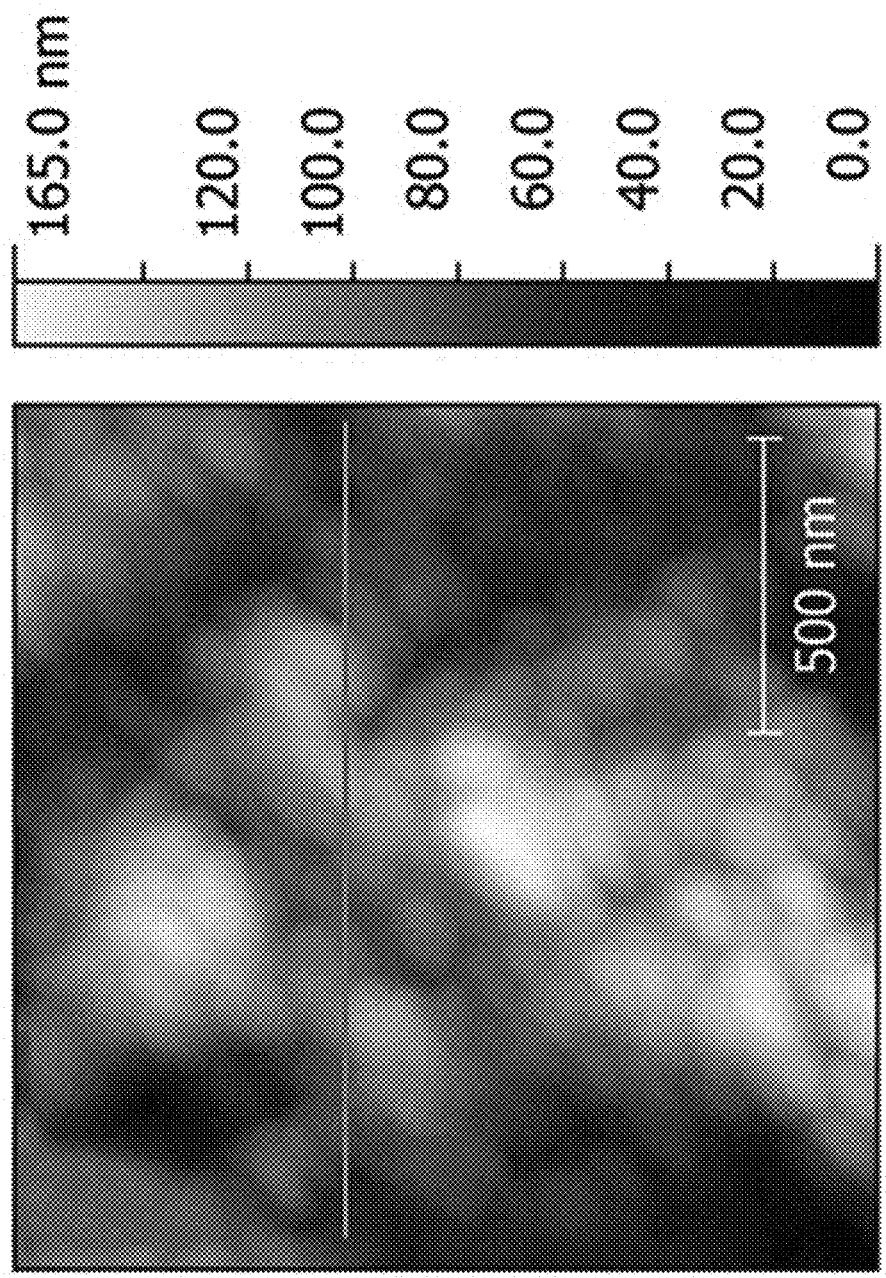
FIG. 20 is a photograph showing the surface morphology of the thin film obtained from FIG. 18.

FIG. 20 shows the results of analyzing the particle size of the obtained MOFs using AFM and optical image.

The method according to example embodiments suggests a rapid synthesis of a nano-sized supramolecular metal-organic framework hybrid material, which suggests a developing method for industrial mass production.

Figure 15:
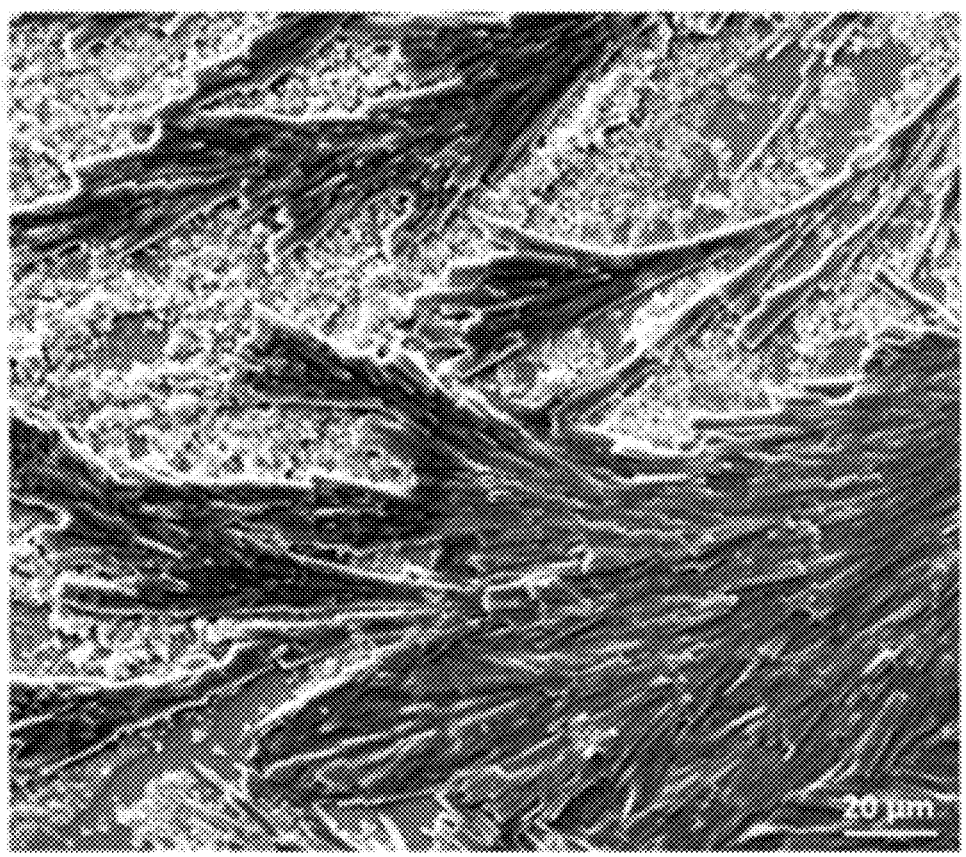
FIG. 15 is a photograph showing that a gel becomes a spherical nano-sized metal-organic framework hybrid particle impregnated in the hybrid fiber when the supramolecular metal-organic framework hybrid gel (MOG) is dried at room temperature for a long time.

FIG. 15 is a photograph showing that the gel becomes a spherical nano-sized metal-organic framework hybrid particle impregnated in the hybrid fiber when the metal-organic framework hybrid gel (MOG) obtained from the example embodiments is dried at room temperature for a long time.

Figure 16:
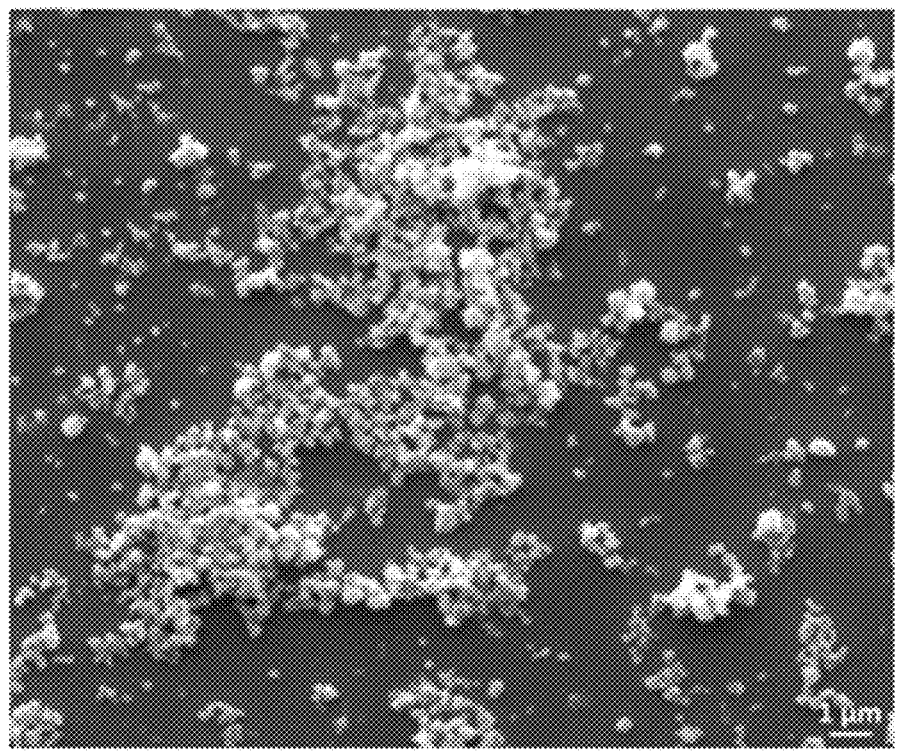
FIG. 16 is a photograph showing that fibers of a gel are all broken by immersing the gel shown in FIG. 15 in a polar organic solvent for less than one minute to produce pure metal-organic framework nanocrystals.

FIG. 16 is a photograph showing that gel fibers are all broken to produce a pure metal-organic framework nanocrystal when the gel shown in FIG. 15 is immersed in a polar organic solvent, for example, methanol, for less than 1 minute.

In other words, when the metal-organic framework hybrid gel is produced according to example embodiments and then dried or cleaned after drying, the metal-organic framework hybrid nanoparticles may be rapidly and easily fabricated.

8. Thin Film Fabrication Enabled by Supramolecular Metal-Organic Gels

Apart from unique physical properties of the supramolecular MOF hybrid material discussed above, another advantages of the sol-gel phase lies in the ease of fabrication of the supramolecular MOF hybrid thin film.

Uniformity in nanosized crystal size contributes to uniform, compact, and flat thin films.

The thin film may be easily fabricated on any support using the known coating methods, for example, dip coating, spin coating, and doctor-blade film coating methods. As the support, a glass, silicon, ITO (Indium Tin Oxide), or FTO substrate or the like may be used, but is not limited thereto.

For example, the fibrous network of the gel is broken down by adding a solvent, for example, methanol, into the obtained G⊃MEH gel to provide pure nanoparticles, and the thin film of nanoparticles may be obtained by dip coating the obtained solution including nanoparticles onto the surface of a glass substrate and the like.

On the other hand, the thin film may be fabricated in the different thickness (a thickness of 100 nm to 10 μm) according to the concentration of the nanoparticle suspension.

Figure 17:
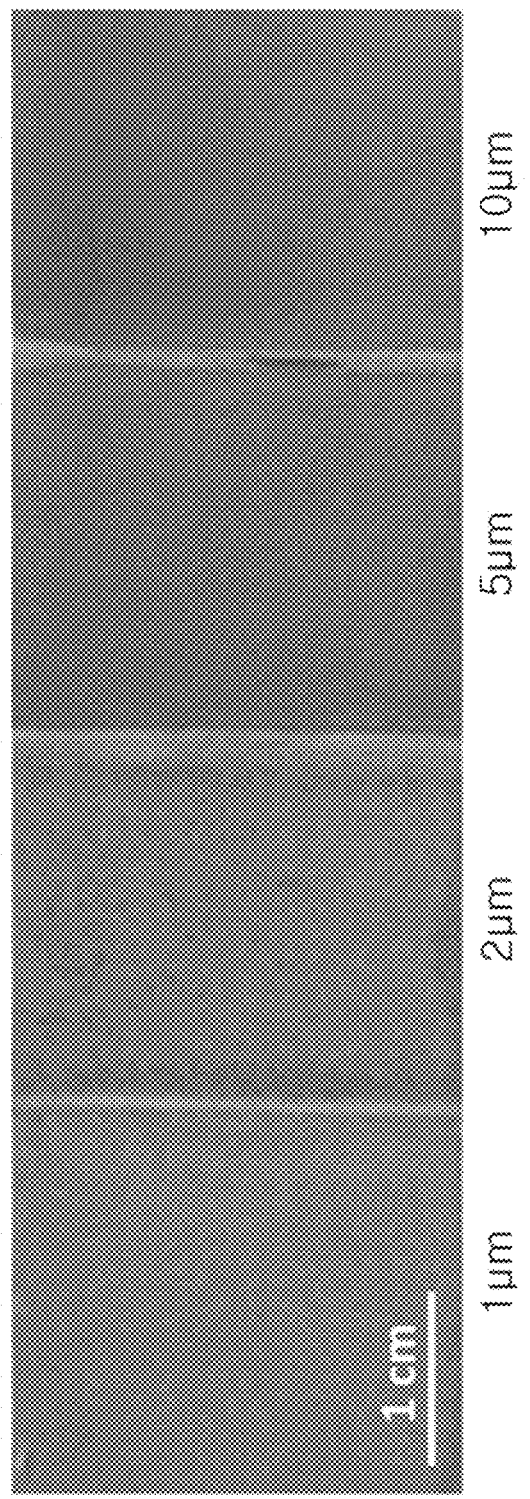
FIG. 17 is a photograph showing a MOF thin film deposited on a glass substrate obtained by a sol-gel method, having an increasing thickness from left to right.

In example embodiments, the nanoparticle suspension is coated on a glass substrate by the doctor blade method while adjusting the concentration to provide thin films having a thickness of 1 μm, 2 μm, 5 μm, and 10 μm, and photographs of each of the obtained films are shown in FIG. 17.

Figure 18:
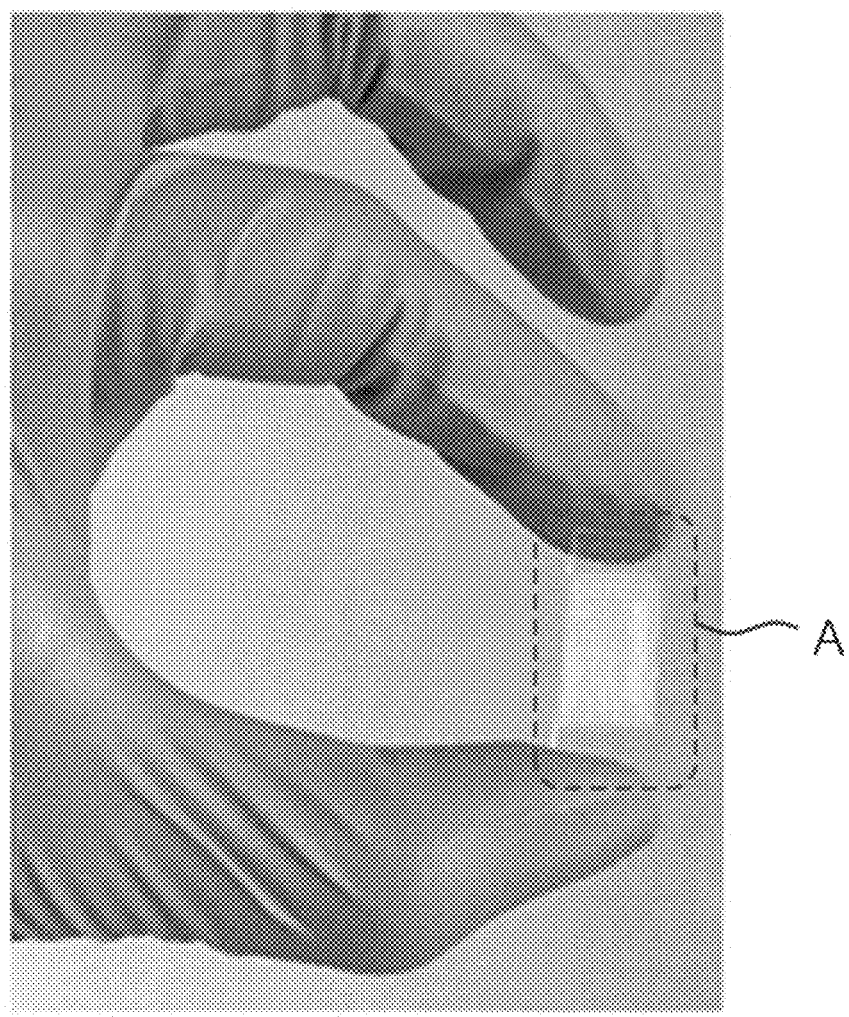
FIG. 18 is a photograph showing a MOF thin film deposited on a glass substrate by dip coating a supramolecular metal-organic framework nanoparticle suspension.

On the other hand, the sol phase of G⊃DMSO may more easily fabricate a very compact and uniform thin coating of these hybrid materials. The air-dried coating is rapidly cleaned by carefully dipping in methanol for about 10 to 15 minutes to remove an undesirable water-soluble precursor for obtaining a pure metal-organic framework nanoparticle film. Thereby, the photograph of the obtained thin film is shown in FIG. 18. The part marked as A of FIG. 18 is a thin film formed on the glass substrate.

Figure 19:
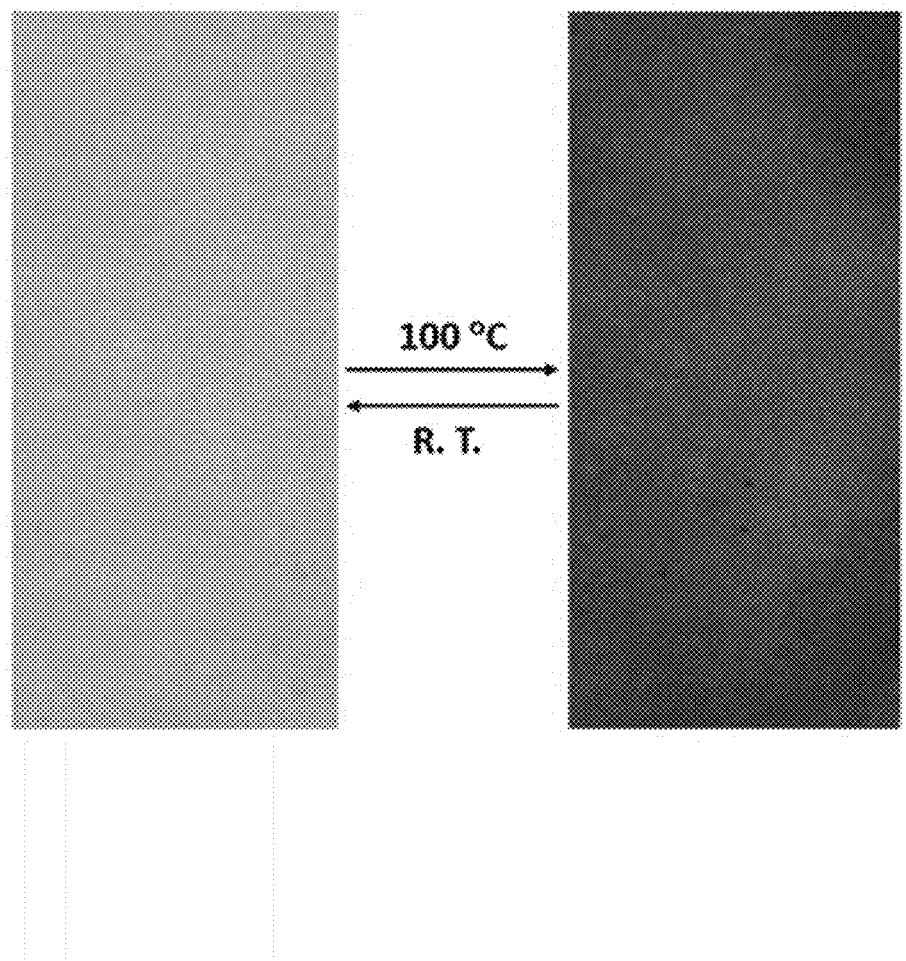
FIG. 19 is photographs showing that the color is reversibly changed according to heating the thin film obtained from FIG. 18 at 100° C. and then cooling the same at room temperature.

When the thin film marked as A of FIG. 18 is not cleaned, it is colored green when heating at a high temperature; on the other hand, the cleaned thin film changes color from blue green to dark blue by removing coordinated water from the central copper, which is the expected typical color change in the HKUST-1 thin film (referred to FIG. 19).

The obtained thin film has high uniformity, for example, surface roughness ranging from about 10 nm to about 30 nm in an average particle diameter of less than or equal to about 100 nm, for example, less than or equal to about 30 nm.

Specifically, the surface morphology of the thin film is shown in FIG. 20.

From FIG. 20, it is understood that the nanoparticles present in the thin film have a size of less than or equal to about 30 nm.

Figure 21:
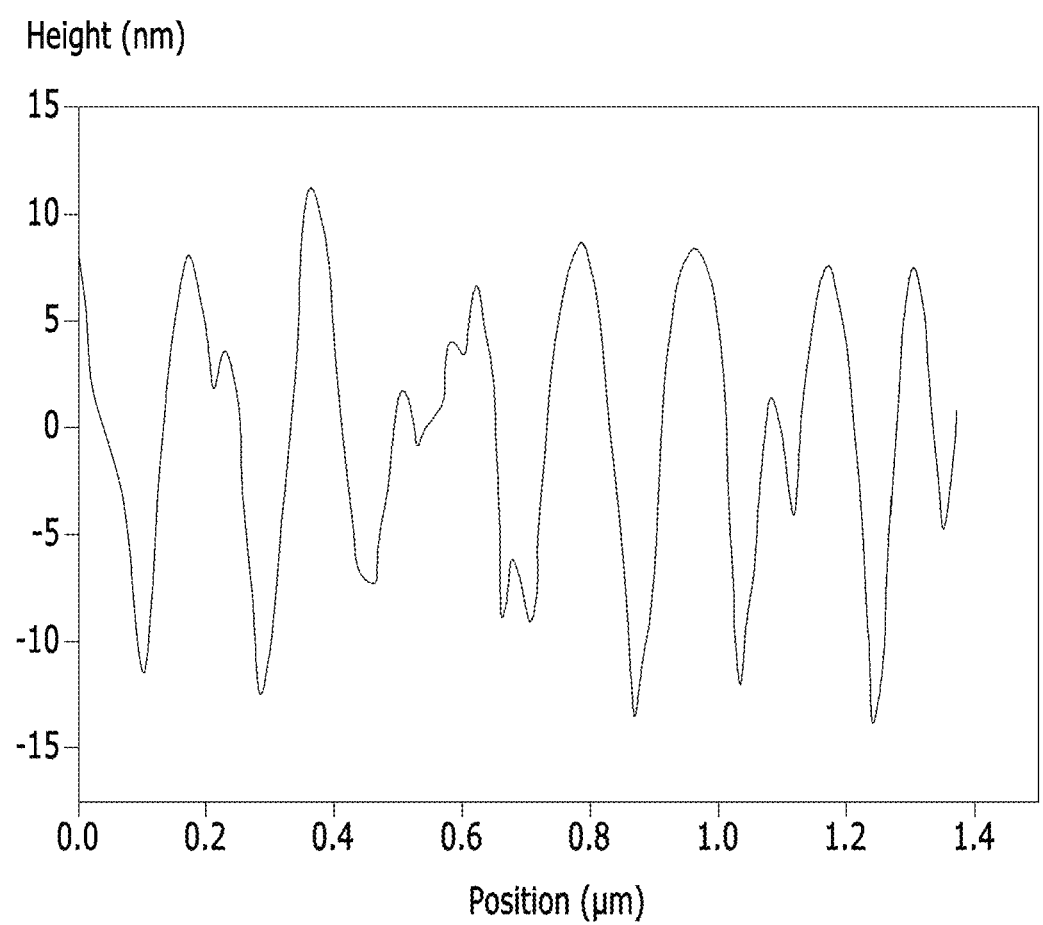
FIG. 21 is a profile in which surface roughness of a region shown on a horizontal line in FIG. 20 is analyzed by AFM topography.

FIG. 21 is a graph showing the surface roughness of the region shown in the horizontal line of FIG. 20 measured by an AFM topographical scan.

From FIG. 21, it is understood that the obtained film has surface roughness ranging from about 10 nm to about 30 nm, which shows that a very uniform thin film is formed.

Figure 22:
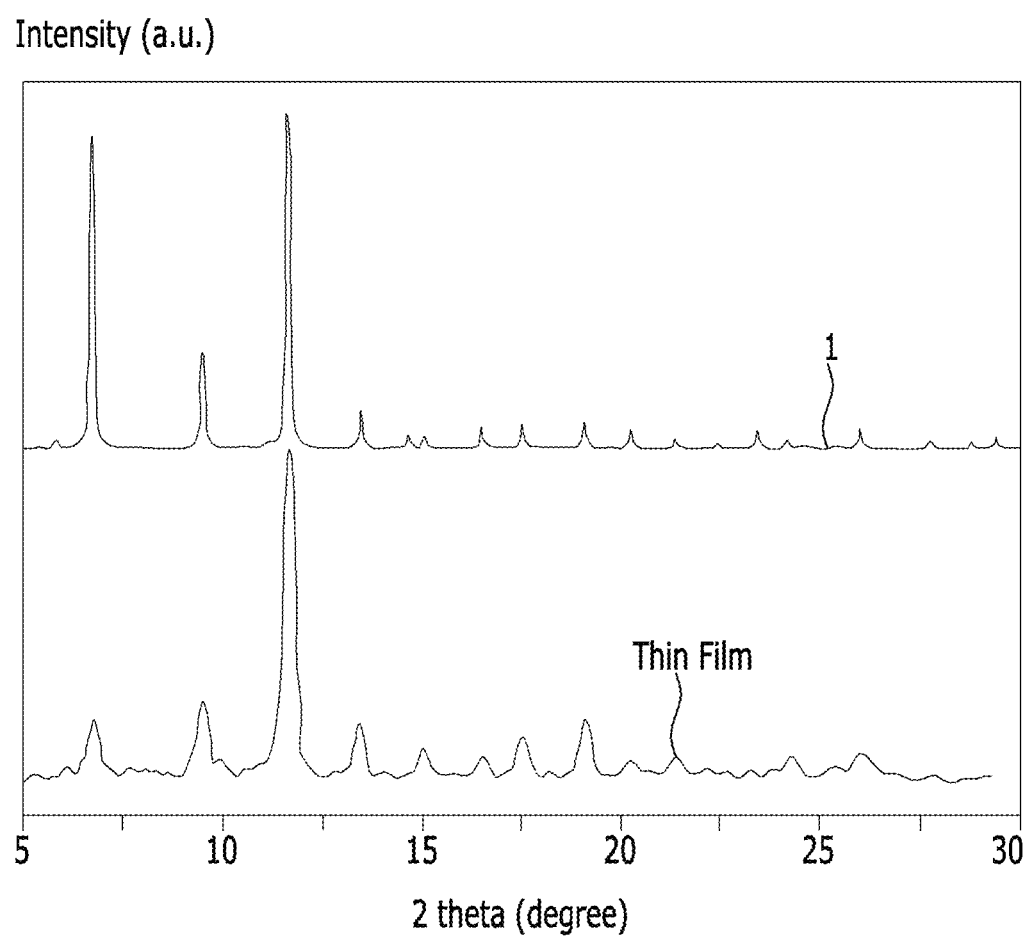
FIG. 22 is 2D X-ray diffraction graphs confirming a crystalline structure of the thin film obtained from FIG. 18, wherein the lower graph shows a 2D X-ray diffraction graph of the thin film itself which is not deposited with the supramolecular metal-organic framework nanoparticle, and the graph marked with 1 is a graph of simulating 2D X-ray diffraction of a thin film deposited with a supramolecular metal-organic framework nanoparticle.

FIG. 22 is a 2D X-ray diffraction graphs confirming a crystalline structure of nanoparticles in the thin film, wherein the lower graph is a 2D X-ray diffraction graph of the thin film itself in which nanoparticles are not deposited, and the graph marked with 1 is a graph simulating a 2D X-ray diffraction of the thin film deposited with nanoparticles.

The following examples illustrate this disclosure in more detail. However, it is understood that this disclosure is not limited by these examples.

In the present application, the samples of metal-organic gels, supramolecular metal-organic framework hybrid nanoparticles and so on, which are used in order to explain supramolecular metal-organic framework (MOF) materials, are fabricated according to the following Examples, and each of the tests and analysis is performed according to the following Experimental Examples, unless otherwise described in the present application. However, example embodiments are not limited thereto.

EXAMPLES

Example 1

Fabrication of a Metal-Organic Gel (G⊃MEH) and a Supramolecular Metal-Organic Framework Hybrid Nanoparticle Thereof 1,3,5-benzenetricarboxylic acid (BTC) is dissolved in methanol to be 2 mM solution, and then triethylamine is added thereto to be 6 mM solution, in order to achieve completely dissolved ligand in the solvent. This solution is sonicated for 5 minutes. Then, copper nitrate solution is prepared in methanol to be 3 mM solution by dissolving copper nitrate in methanol and applying with sonication for 1 to 2 minutes.

A mixture is made by adding the copper nitrate solution to the solution having completely dissolved ligand with vigorous shaking for a few seconds. The mixture is then left undisturbed until it shows gel-like behaviour, as confirmed by the tube inversion method. The mixture shows gel-like behaviour when it is left for about 2 minutes. Thereafter, a metal-organic gel (G⊃MEH) is fabricated.

The metal-organic gel (G⊃MEH) is dried at room temperature. The dried metal-organic gel (G⊃MEH) is immersed in methanol for less than 1 minute and then washed. Thereafter, a supramolecular metal-organic framework hybrid nanoparticle derived from G⊃MEH is formed.

Example 2

Fabrication of a Metal-Organic Gel (G⊃ETH) and a Supramolecular Metal-Organic Framework Hybrid Nanoparticle Thereof A metal-organic gel (G⊃ETH) and a supramolecular metal-organic framework hybrid nanoparticle derived from G⊃ETH are obtained through the same process as in Example 1, except that ethanol is used instead of methanol when the solution, which has completely dissolved ligand, is prepared and when the copper nitrate solution is prepared. Herein, the mixture shows gel-like behaviour when it is left for about 5 minutes.

Example 3

Fabrication of a Metal-Organic Gel (G⊃ACN) and a Supramolecular Metal-Organic Framework Hybrid Nanoparticle Thereof A metal-organic gel (G⊃ACN) and a supramolecular metal-organic framework hybrid nanoparticle derived from G⊃ACN are obtained through the same process as in Example 1, except that acetonitrile is used instead of methanol when the solution, which has completely dissolved ligand, is prepared and when the copper nitrate solution is prepared. Herein, the mixture shows gel-like behaviour when it is left for about 5 minutes.

Example 4

Fabrication of a Metal-Organic Gel (G⊃DMF) and a Supramolecular Metal-Organic Framework Hybrid Nanoparticle Thereof A metal-organic gel (G⊃DMF) and a supramolecular metal-organic framework hybrid nanoparticle derived from G⊃DMF are obtained through the same process as in Example 1, except that N,N-dimethyl formamide is used instead of methanol when the solution, which has completely dissolved ligand, is prepared and when the copper nitrate solution is prepared.

Herein, the mixture shows gel-like behaviour when it is left for about 10 minutes.

Example 5

Fabrication of a Metal-Organic Gel (G⊃DMSO) and a Supramolecular Metal-Organic Framework Hybrid Nanoparticle Thereof A metal-organic gel (G⊃DMSO) and a supramolecular metal-organic framework hybrid nanoparticle derived from G⊃DMSO are obtained through the same process as in Example 1, except that dimethyl sulfoxide is used instead of methanol when the solution, which has completely dissolved ligand, is prepared and when the copper nitrate solution is prepared.

Herein, the mixture shows gel-like behaviour when it is left for about 20 minutes.

Example 6

Fabrication of a Thin Film

The metal-organic gel (G⊃MEH) material obtained from the Example 1 is used as precursors for fabricating a MOF thin film. The metal-organic gel (G⊃MEH) material is washed three times using 20 ml of methanol and then centrifuged to collect the NMOF particles.

Suspension remained at the bottom of the centrifuge tube is collected and later used to deposit a thin film of MOF onto a glass substrate via the doctor blade technique, with varying gap size set between the tip of the blade and the surface of the glass substrate from a few microns up to 10 s of microns, particularly from 4 μm up to 50 μm. The same NMOF suspension is also successfully used for dip coating and spin coating methods [step wise: (i) 500 rpm for 50 s, (ii) 800 rpm for 50 s, and (iii) 1000 rpm for 20 s].

Example 7

Fabrication of a Thin Film

A thin film is obtained through the same process as in Example 6, except that the metal-organic gel (G⊃ETH) fabricated in Example 2 is used instead of the metal-organic gel (G⊃MEH) fabricated in Example 1.

Example 8

Fabrication of a Thin Film

A thin film is obtained through the same process as in Example 6, except that the metal-organic gel (G⊃ACN) fabricated in Example 3 is used instead of the metal-organic gel (G⊃MEH) fabricated in Example 1.

Example 9

Fabrication of a Thin Film

A thin film is obtained through the same process as in Example 6, except that the metal-organic gel (G⊃DMF) fabricated in Example 4 is used instead of the metal-organic gel (G⊃MEH) fabricated in Example 1.

Example 10

Fabrication of a Thin Film

A thin film is obtained through the same process as in Example 6, except that the metal-organic gel (G⊃DMSO) fabricated in Example 5 is used instead of the metal-organic gel (G⊃MEH) fabricated in Example 1.

Comparative Examples 1 to 5

The reactions are performed through the same processes as in Examples 1 to 5, respectively, except that NaOH is used instead of triethylamine.

Herein, precipitation products instead of metal-organic gels are prepared when the reaction mixtures are left standing.

The reactions performed refer to Comparative Examples 1 to 5 in sequence.

Comparative Examples 6 to 10

The reactions are performed through the same processes as in Examples 1 to 5, respectively, except that KOH is used instead of triethylamine.

Herein, precipitation products instead of metal-organic gels are prepared when the reaction mixtures are left standing.

The reactions performed refer to Comparative Examples 6 to 10 in sequence.

Experimental Example 1

Rheological Measurement

Rheological measurements including storage modulus, loss modulus and so on are performed on the Physica MCR-301 (Anton Paar) rheometer equipped with a temperature controlled basal plate. Parallel plate configuration is used for all studies by keeping a 1 mm gap distance between the basal and the top plates. A constant shear stress of 10 Pa is applied for creep and stress recovery tests.

Experimental Example 2

Scanning Electron Microscope (SEM)

Gel specimens are coated with a thin layer of gold using the SC7620 Polaron sputter coater (Quorum Technologies). Then, the coated gel specimens are photographed using the scanning electron microscope (Carl Zeiss EVO LS15).

Experimental Example 3

Infinite Focus Microscopy (IFM)

Optical images and surface height topography of MOF thin films are characterized using infinite focus microscopy (IFM, Alicona InfiniteFocus 3D profilometer).

Experimental Example 4

X-Ray Diffraction Analysis

X-ray powder diffraction characterization of nanoparticles and gel samples are performed using the Rigaku Smart Lab diffractometer with Cu Kα source (1.541 Å); diffraction data are collected at 2θ angle from 2° to 30°, using a 0.01° step size and 1°/min step speed.

Experimental Example 5

Atomic Force Microscopy (AFM)

Atomic force microscopy (AFM) height topography and AM-FM tapping mode imaging are carried out using the Asylum Research MFP-3D AFM in air. A silicon AFM probe (Tap300-G, Budget Sensor) with a resonant frequency of 300 kHz and a force constant of 40 N/m mounted on the AM-FM cantilever holder is used for nanomechanical characterization; the tip calibration is performed using a standard sample of Matrimid®5218 with an established Young's modulus (E=4 GPa).

Experimental Example 6

Electrical Conductivity Test

Electrical conductivity of gel samples are measured using the Keithley 2614B sourcemeter and a custom designed conductivity cell lined with aluminium electrodes spaced at 1 cm apart.

Figure 23:
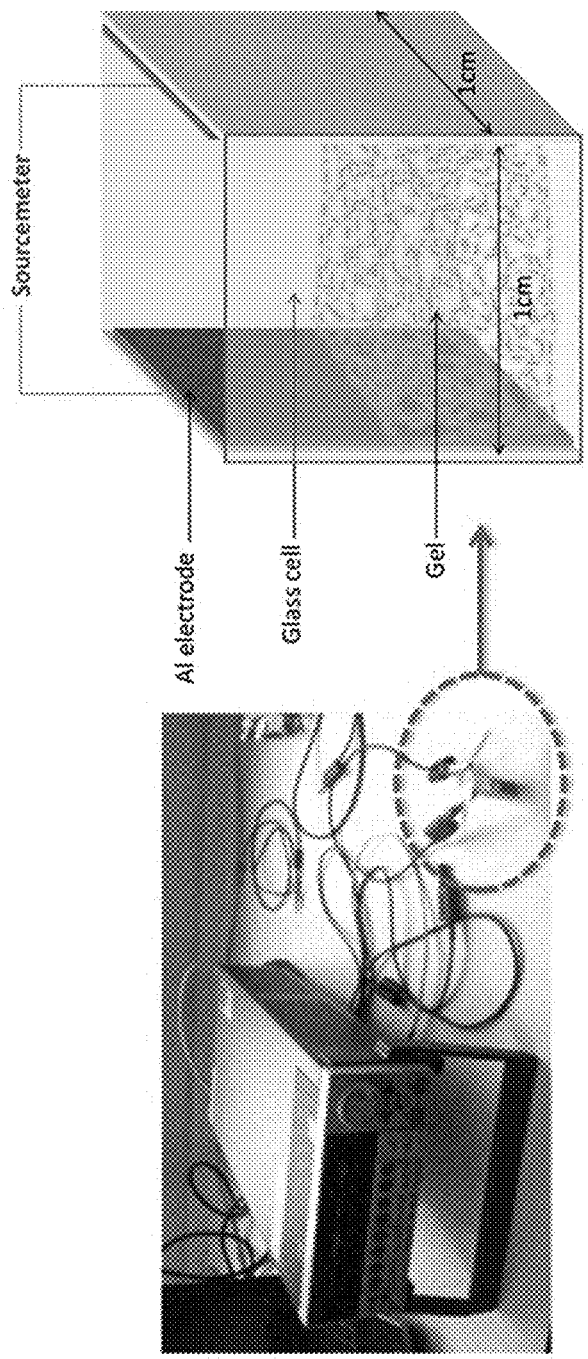
FIG. 23 is an experimental setup and geometry of the test cell used in electrical conductivity measurements of the supramolecular MOF hybrid gel (MOG).

FIG. 23 is an experimental setup and geometry of a test cell used in electrical conductivity measurements.

The conductivity of the visco-elastic solid is measured from a thin layer of the visco-elastic material derived from G⊃ACN sandwiched between a pair of flat aluminium electrodes.

While this disclosure has been described in connection with what is presently considered to be practical example embodiments, it is to be understood that the inventive concepts are not limited to the disclosed embodiments, but, on the contrary, is intended to cover various modifications and equivalent arrangements included within the spirit and scope of the appended claims.

What is claimed is:

1. A supramolecular metal-organic framework material consisting essentially of:
a reaction product of copper nitrate ($Cu(NO_3)_2$), a trialkylamine represented by Chemical Formula 1, and a benzene substituted with 3 carboxyl groups in a non-aqueous solvent that is an organic solvent and does not include water,

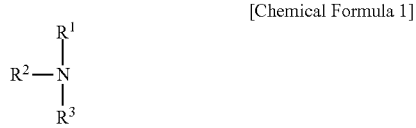

[Chemical Formula 1]

wherein in Chemical Formula 1,
each of $R^1$, $R^2$, and $R^3$ are the same or different and are independently a $C_1$ to $C_{10}$ alkyl group,
wherein the copper nitrate ($Cu(NO_3)_2$) is in a form of a Cu(II) solution formed in the non-aqueous solvent,
wherein the supramolecular metal-organic framework material is in a gel state, and wherein a molar concentration of the trialkylamine represented by Chemical Formula 1 in the non-aqueous solvent is greater than a molar concentration of the copper nitrate in the non-aqueous solvent when forming the reaction product, and
the molar concentration of the copper nitrate in the non-aqueous solvent is greater than a molar concentration of the benzene substituted with 3 carboxyl groups in the non-aqueous solvent when forming the reaction product.

2. A supramolecular metal-organic framework material consisting essentially of:
a reaction product of copper nitrate ($Cu(NO_3)_2$), triethylamine ($NEt_3$), and 1,3,5-benzenetricarboxylic acid (BTC) in a non-aqueous solvent that is an organic solvent and does not include water,
wherein the non-aqueous solvent includes one of a $C_1$-$C_{10}$ alkanol, dimethyl sulfoxide (DMSO), N,N-dimethyl formamide (DMF), N,N-diethylformamide (DEF), N,N-dimethylacetimide (DMAc), acetonitrile (ACN), toluene, dioxane, chlorobenzene, methylethylketone (MEK), pyridine, or a combination thereof,
wherein the supramolecular metal-organic framework material is in a gel state, and wherein a molar concentration of the $NEt3$ in the non-aqueous solvent is greater than a molar concentration of the copper nitrate in the non-aqueous solvent when forming the reaction product, and
the molar concentration of the copper nitrate in the non-aqueous solvent is greater than a molar concentration of the BTC in the non-aqueous solvent when forming the reaction product.

3. The supramolecular metal-organic framework material of claim 1, wherein
the trialkylamine represented by the Chemical Formula 1 is triethylamine ($NEt_3$), and
the benzene substituted with 3 carboxyl groups is 1,3,5-benzenetricarboxylic acid (BTC).

4. The supramolecular metal-organic framework material of claim 1, wherein the non-aqueous solvent includes one of a $C_1$-$C_{10}$ alkanol, dimethyl sulfoxide (DMSO), N,N-dimethyl formamide (DMF), N,N-diethylformamide (DEF), N,N-dimethylacetimide (DMAc), acetonitrile (ACN), toluene, dioxane, chlorobenzene, methylethylketone (MEK), pyridine, or a combination thereof.

5. The supramolecular metal-organic framework material of claim 1, which is capable of undergoing sol-gel transitions upon subsequent alternate additions of the copper nitrate ($Cu(NO_3)_2$) and the benzene substituted with 3 carboxyl groups.

6. The supramolecular metal-organic framework material of claim 1, which is capable of transforming into a sol state when being subjected to a mechanical force.

7. The supramolecular metal-organic framework material of claim 1, wherein the supramolecular metal-organic framework material in a sol state transforms into a gel state again by any of a heat-treatment, an ultrasonification, and an allowance to stand.

8. The supramolecular metal-organic framework material of claim 1, which is capable of transforming into nanoparticles by drying or immersing in a polar organic solvent.

9. The supramolecular metal-organic framework material of claim 1, wherein the supramolecular metal-organic framework material has a lamella structure.

10. A method of preparing the supramolecular metal-organic framework material, of claim 2 the method comprising:

reacting copper nitrate (Cu(NO$_3$)$_2$), triethylamine (NEt$_3$), and 1,3,5-benzenetricarboxylic acid (BTC) in a non-aqueous solvent that is an organic solvent and does not include water, wherein the non-aqueous solvent includes one of a C$_1$-C$_{10}$ alkanol, dimethyl sulfoxide (DMSO), N,N-dimethyl formamide (DMF), N,N-diethyl formamide (DEF), N,N-dimethylacetimide (DMAc), acetonitrile (ACN), toluene, dioxane, chlorobenzene, methylethylketone (MEK), pyridine, and a combination thereof, and wherein a molar concentration of the NEt$_3$ in the non-aqueous solvent is greater than a molar concentration of the copper nitrate solution in the non-aqueous solvent when forming the reaction product, and the molar concentration of the copper nitrate solution in the non-aqueous solvent is greater than a molar concentration of the BTC in the non-aqueous solvent when forming the reaction product.

11. The method of claim 10, wherein:

the reacting reacts a solution including the copper nitrate (Cu(NO$_3$)$_2$) with a solution including the triethylamine (NEt$_3$) and 1,3,5-benzenetricarboxylic acid (BTC).

12. The method of claim 10, further comprising:

subsequently alternately adding the copper nitrate (Cu(NO$_3$)$_2$) and the BTC to cause sol-gel transitions of the supramolecular metal-organic framework material.

13. The method of claim 10, further comprising:

applying mechanical force to the supramolecular metal-organic framework material to cause a transition into a sol state.

14. The method of claim 13, further comprising:

one of heat-treating, ultrasonificating, and standing the supramolecular metal-organic framework material in a sol state to transform it into a gel state again.

15. A molded article comprising the supramolecular metal-organic framework material of claim 2.

16. The molded article of claim 15, wherein the molded article is a film.

17. An electronic device comprising the molded article of claim 15.

18. A supramolecular metal-organic framework material in a fiber phase comprising:

the supramolecular metal-organic framework material of claim 2, wherein the reaction product is formed in the non-aqueous solvent without adding water to the non-aqueous solvent during a reaction to form the reaction product, and the non-aqueous solvent includes one of dimethyl sulfoxide (DMSO), N,N-dimethyl formamide (DMF), acetonitrile (ACN), methanol, or ethanol.

19. The supramolecular metal-organic framework material of claim 1, wherein the supramolecular metal-organic framework material consists of the reaction product of the copper nitrate (Cu(NO$_3$)$_2$), the trialkylamine represented by Chemical Formula 1, and the benzene substituted with 3 carboxyl groups in the non-aqueous solvent that is an organic solvent and does not include water.

20. The supramolecular metal-organic framework material of claim 2, wherein the supramolecular metal-organic framework material consists of the reaction product of the copper nitrate (Cu(NO$_3$)$_2$), the triethylamine (NEt$_3$), and the 1,3,5-benzenetricarboxylic acid (BTC) in the non-aqueous solvent that is an organic solvent and does not include water.

* * * * *